US006284458B1

(12) United States Patent
Anderson et al.

(10) Patent No.: US 6,284,458 B1
(45) Date of Patent: Sep. 4, 2001

(54) COMPOSITIONS AND METHODS FOR TREATMENT OF HEPATITIS C VIRUS-ASSOCIATED DISEASES

(75) Inventors: Kevin P. Anderson, Carlsbad; Ronnie C. Hanecak, San Clemente, both of CA (US); Kazuya Hoshiko, Koshi-machi (JP); Chikateru Nozaki; Tsukasa Nishihara, both of Kumamoto (JP); Hiroshi Nakatake, Kikuyo-machi (JP); Fukusaburo Hamada, Nishigoshi-machi (JP); Tatsuo Eto, Ohzu-machi (JP); Shinichi Furukawa, Koshi-machi (JP)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/397,220

(22) PCT Filed: Sep. 10, 1993

(86) PCT No.: PCT/JP93/01293

§ 371 Date: Mar. 9, 1995

§ 102(e) Date: Mar. 9, 1995

(87) PCT Pub. No.: WO94/05813

PCT Pub. Date: Mar. 17, 1994

(30) Foreign Application Priority Data

Apr. 14, 1993 (JP) .................................................. 5-087195

(51) Int. Cl.[7] .............................. C12Q 1/68; C07H 21/04; C12N 15/85
(52) U.S. Cl. .............................. 435/6; 435/325; 435/366; 536/23.1; 536/24.5
(58) Field of Search .......................... 435/6, 91.31, 172.1, 435/172.3, 240.2, 320.1, 325, 366; 536/23.1, 23.2, 24.5; 514/44

(56) References Cited

U.S. PATENT DOCUMENTS

| 5,610,054 | * | 3/1997 | Draper | ................................ | 435/363 |
| 5,714,596 | | 2/1998 | Houghton et al. | ................ | 536/23.72 |
| 5,922,857 | | 7/1999 | Han et al. | ........................... | 536/24.1 |

FOREIGN PATENT DOCUMENTS

| 0 318 216 | | 5/1989 | (EP) . |
| 388232 | * | 9/1990 | (EP) . |
| 9219743 | * | 11/1992 | (WO) . |

OTHER PUBLICATIONS

Branch TIBS 23:45–50 (Feb. 1998).*
Gewirtz et al. PNAS 93: 3161–3163 (1996).*
Rojauasakul et al. Adv. Drug Delresy Bev 18:115–131, 1996.*

Choo et al., "Genetic organization and diversity of hepatitis C virus," *Proc. Natl. Acad. Sci.* 1991, 88, 2451–2455.

Choo et al., "Isolation of a cDNA clone derived from a blood–borne non–A, non–B viral hepatitis genome," *Science* 1989, 244, 359–362.

Han et al., "Characterization of the terminal regions of hepatitis C viral RNA: Indentification of conserved sequences in the 5' untranslated region and poly(A) tails at the 3' end," *Proc. Natl. Acad. Sci.* 1991, 88, 1711–1715.

Inchauspe et al., "Genomic structure of the human prototype strain H of hepatitis C virus: Comparison with American and Japanese isolates," *Proc. Natl. Acad. Sci.* 1991, 88, 10292–10296.

Inoue, et al., "Synthesis and hybridization studies on two complementary nona (2'–O–methyl) ribonucleotides," *Nucleic Acids Research* 1991, 15:6131–6148.

Nielsen et al., "Sequence–selective recognition of DNA by strand displacement with a thymine–substituted polyamide," *Science* 1991, 254:1497–1500.

Rothenberg et al., "Oligodeoxynucleotides as anti–sense inhibitors of gene expression: therapeutic implications," *J. Natl. Cancer Inst.* 1989, 81:1539–1544.

Sproat et al., "New synthetic routes to protected purine 2'–O–methylriboside–3'–O–phosphoramidites using a novel alkylation procedure," *Nucleic Acids Research* 18:41–49 (1990).

Takamizawa et al., "Structure and organization of the hepatitis C virus genome isolated from human carriers," *J. Virol.* 1991, 65:1105–1113.

Tsukiyama–Kohara et al., "Internal ribosome entry site within hepatitis C virus RNA," *J. Virol.* 1992, 66:1476–1483.

Zon, G., "Oligonucleotide analogues as potential chemotherapeutic agents," *Pharmaceutical Res.* 1987, 5:539–549.

* cited by examiner

*Primary Examiner*—Andrew Wang
(74) *Attorney, Agent, or Firm*—Licata & Tyrrell P.C.

(57) ABSTRACT

Antisense oligonucleotides are provided which are complementary to and hybridizable with at least a portion of HCV RNA and which are capable of inhibiting the function of the HCV RNA. These oligonucleotides can be administered to inhibit the activity of Hepatitis C virus in vivo or in vitro. These compounds can be used either prophylactically or therapeutically to reduce the severity of diseases associated with Hepatitis C virus, and for diagnosis and detection of HCV and HCV-associated diseases. Methods of using these compounds are also disclosed.

6 Claims, 9 Drawing Sheets

GCCAGCCCCCGAUUGGGGGCGACACUCCACCAUAGAUCACUCCCCUGUGAGGAACUACUGUCUUCACGCAG
AAAGCGUCUAGCCAUGGCGUUAGUAUGAGUGUCGUGCAGCCUCCAGGACCCCCCUCCCGGGAGAGCCAUA
GUGGUCUGCGGAACCGGUGAGUACACCGGAAUUGCCAGGACGACCGGGUCCUUUCUUGGAUCAACCCGCTC
AAUGCCUGGAGAUUUGGGCGUGCCCCCGCGAGACUGCUAGCCGAGUAGUGUUGGGUCGCGAAAGGCCUUGU
GGUACUGCCUGAUAGGGUGCUUGCGAGUGCCCCGGGAGGUCUCGUAGACCGUGCACCAUGAGCACGAAUCC
UAAACCUCAAAGAAAAACCAAACGUAACACCAACCGCCGCCCACAGGAGGUCAAGUUCCCGGGCGGUGGUC
AGAUCGUUGGUGGAGUUUACCUGUUGCCGCGCAGGGGCCCCAGGUUGGGUGUGCGCGCGAUCAGGAAGACU
UCCGAGCGGUCGCAACCCCGUGGAAGGCGACAGCCUAUCCCCAAGGCUCGCCGGCCCGAGGGCAGGGCCUG
GGCUCAGCCCGGGUAUCCUUGGCCCCUCUAUGGCAAUGAGGGCAUGGGGUGGGCAGGAUGGCUCCUGUCAC
CCCGCGGCUCCCGGCCUAGUUGGGGCCCCACGGACCCCCGGCGUAGG

FIG. 1

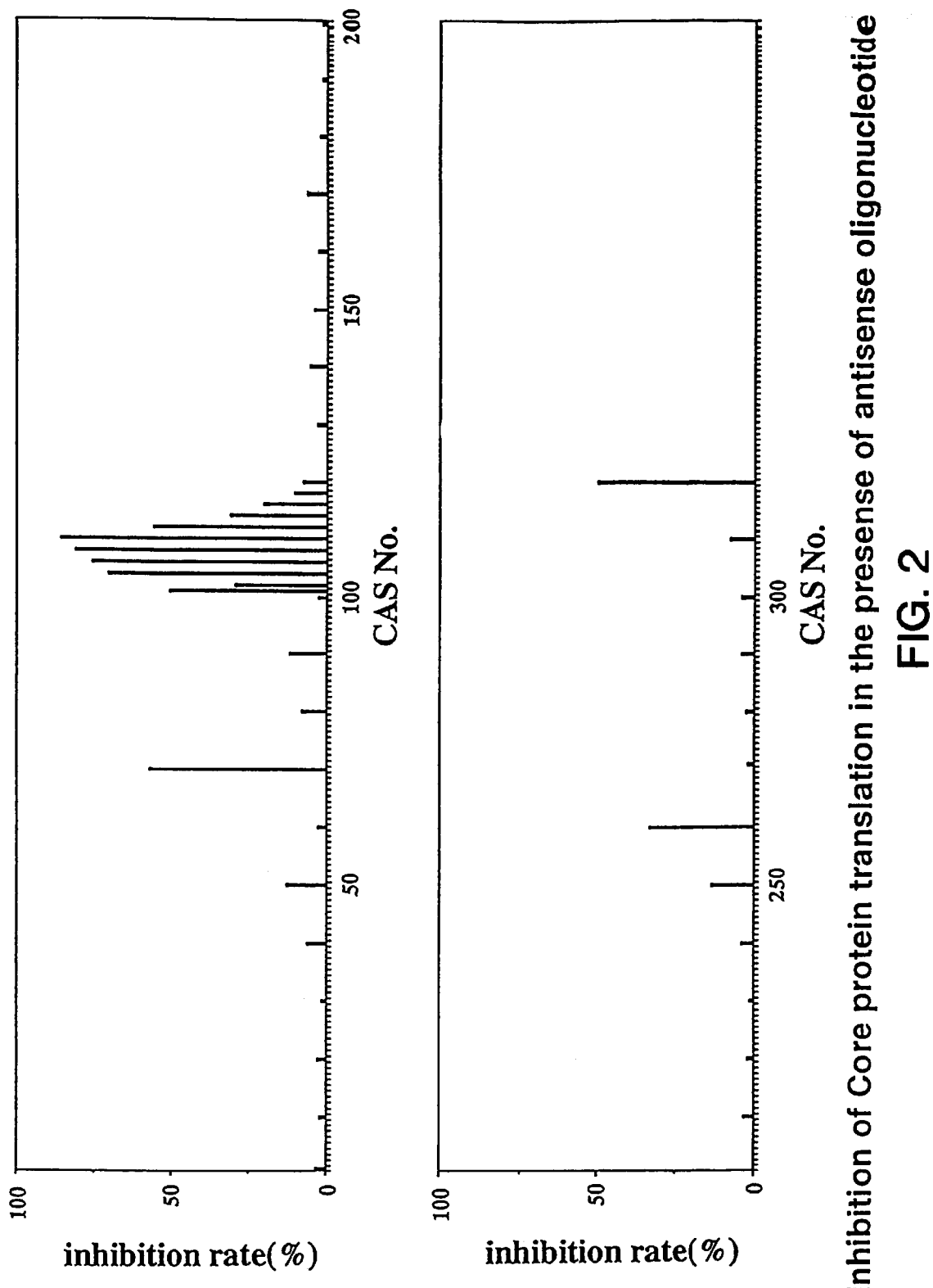

Influence of oligo. sequence and RNA length on in vitro translation

RNA709 : from Cla I-digested pGEM NCE1 plasmid
RNA1375 : from Bam HI-digested pGEM NCE1 plasmid

US 6,284,458 B1

COMPOSITIONS AND METHODS FOR TREATMENT OF HEPATITIS C VIRUS-ASSOCIATED DISEASES

FIELD OF THE INVENTION

This invention relates to the design and synthesis of antisense oligonucleotides which can be administered to, inhibit the replication of Hepatitis C virus in vivo or in vitro and to treat Hepatitis C virus-associated disease. These compounds can be used either prophylactically or therapeutically to reduce the severity of diseases associated with Hepatitis C virus. Oligonucleotides which are specifically hybridizable with RNA targets are disclosed.

BACKGROUND OF THE INVENTION

The predominant form of hepatitis currently resulting from transfusions is not related to the previously characterized Hepatitis A virus or Hepatitis B virus and has been referred to as Non-A, Non-B Hepatitis (NANBH). NANBH currently accounts for over 90% of cases of post-transfusion hepatitis. Estimates of the frequency of NANBH in transfusion recipients range from 5%–13% for those receiving volunteer blood, or 25%–54% for those receiving blood from commercial sources.

Acute NANBH, while often less severe than acute disease caused by Hepatitis A or Hepatitis B viruses, occasionally leads to severe or fulminant hepatitis. Of greater concern, progression to chronic hepatitis is much more common after NANBH than after either Hepatitis A or Hepatitis B infection. Chronic NANBH has been reported in 10%–70% of infected individuals. This form of hepatitis can be transmitted even by asymptomatic patients, and frequently progresses to malignant disease such as cirrhosis and hepatocellular carcinoma. Chronic active hepatitis, with or without cirrhosis, is seen in 44%–90% of posttransfusion hepatitis cases. Of those patients who developed cirrhosis, approximately one-fourth died of liver failure.

Chronic active NANBH is a significant problem to hemophiliacs who are dependent on blood products; 5%–11% of hemophiliacs die of chronic end-stage liver disease. Cases of NANBH other than those traceable to blood or blood products are frequently associated with hospital exposure, accidental needle stick, or tattooing. Transmission through close personal contact also occurs, though this is less common for NANBH than for Hepatitis B.

The causative agent of the majority of NANBH has recently been identified and is now referred to as Hepatitis C Virus (HCV). Houghton et al., EP Publication 318,216; Choo et al., Science 1989, 244, 359–362. Based on serological studies using recombinant DNA-generated antigens it is now clear that HCV is the causative agent of most cases of post-transfusion NANBH. Clones of cDNA prepared from nucleic acid isolated from concentrated virus particles were originally isolated based on their ability to encode polypeptides which reacted with sera from NANBH patients. These clones hybridized with RNA, but not DNA, isolated from infected liver tissue, indicating the presence of an RNA genome. Hybridization analyses and sequencing of the cDNA clones revealed that RNA present in infected liver and particles was the same polarity as that of the coding strand of the cDNAs; in other words, the virus genome is a positive or plus-strand RNA genome. EP Publication 318, 216 (Houghton et al.) disclose partial genomic sequences of HCV-1, and teach recombinant DNA methods of cloning and expressing HCV sequences and HCV polypeptides, techniques of HCV immunodiagnostics, HCV probe diagnostic techniques, anti-HCV antibodies, and methods of isolating new HCV sequences. Houghton et al. also disclose additional HCV sequences and teach application of these sequences and polypeptides in immunodiagnostics, probe diagnostics, anti-HCV antibody production, PCR technology and recombinant DNA technology. The concept of using antisense polynucleotides as inhibitors of viral replication is disclosed, but no specific targets are taught. Oligomer probes and primers based on the sequences disclosed are also provided. EP Publication 419,182 (Miyamura et al.) discloses new HCV isolates J1 and J7 and use of sequences distinct from HCV-1 sequences for screens and diagnostics.

The only treatment regimen shown to be effective for the treatment of chronic NANBH is interferon-α. Most NANBH patients show an improvement of clinical symptoms during interferon treatment, but relapse is observed in at least half of patients when treatment is interrupted. Significant improvements in antiviral therapy are therefore greatly desired.

OBJECTS OF THE INVENTION

It is an object of this invention to provide oligonucleotides which are capable of hybridizing with RNA of HCV to inhibit the synthesis or function of said RNA.

It is another object of this invention to provide oligonucleotides which are capable of hybridizing with RNA of HCV to inhibit replication of the virus.

It is a further object to provide oligonucleotides which can modulate the expression of HCV through antisense interaction with viral RNA.

Yet another object of this invention is to provide methods of prophylaxis, diagnostics and therapeutics for acute or chronic HCV infection.

A further object of this invention is to provide methods of prophylaxis, diagnostics and therapeutics for HCV-associated diseases.

Methods, materials and kits for detecting the presence or absence of HCV or HCV RNA in a sample suspected of containing it are further objects of the invention.

These and other objects will become apparent to persons of ordinary skill in the art from a review of the instant specification and appended claims.

BRIEF DESCRIPTION OF THE DRAWINGS

FIG. 1 is the sequence of nucleotides 1–686 SEQ ID NO: 25 comprising the entire 5'-untranslated region (nucleotides 1–341) and a 145-nucleotide core region sequence.

FIG. 2 is a bar graph showing inhibition of HCV core protein translation by antisense oligonucleotides complementary to the region from nucleotide 1 to 350 of HCV RNA.

SUMMARY OF THE INVENTION

Figure 3:
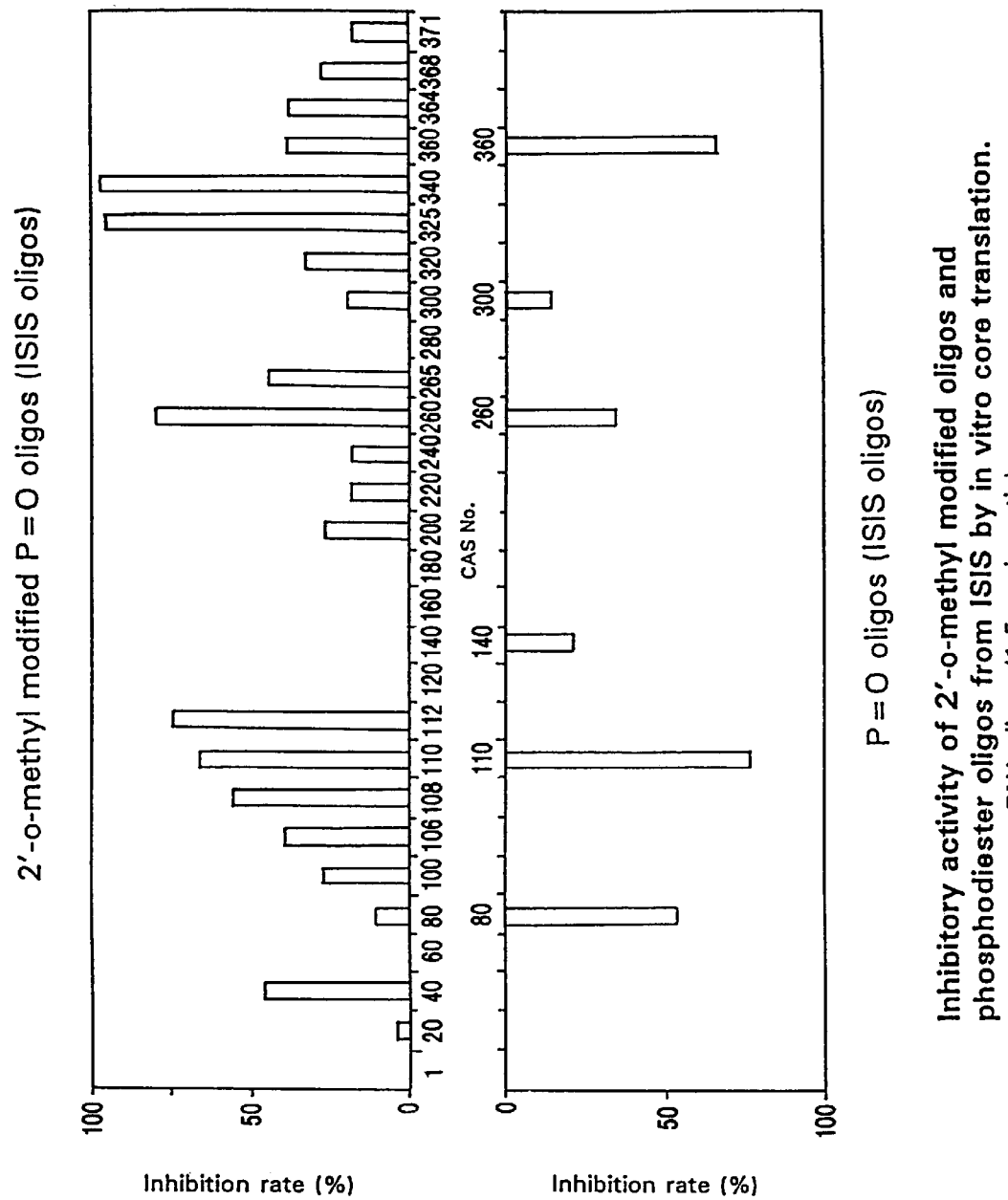
FIG. 3 is a bar graph showing inhibition of HCV core protein translation by 2'-O-methylated antisense oligonucleotides and selected unmodified oligonucleotides of the same sequence.

In accordance with the present invention, compositions and methods for modulating the effects of HCV infection are provided. Oligonucleotides complementary to, and specifically hybridizable with, selected sequences of HCV RNA are provided. The HCV 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence and 3' end hairpin loop are preferred targets. Methods for diagnosing or treating disease states by administering oligonucleotides, either alone or in combination with a pharmaceutically acceptable carrier, to animals suspected of having HCV-associated diseases are also provided.

The relationship between the target RNA and oligonucleotides complementary to at least a portion of the target, and specifically hybridizable with it, is commonly denoted as "antisense". The oligonucleotides are able to inhibit the function of viral RNA by interfering with its replication, transcription into mRNA, translation into protein, packaging into viral particles or any other activity necessary to its overall biological function. The failure of the RNA to perform all or part of its function results in failure of all or a portion of the normal life cycle of the virus.

It has been found that antisense oligonucleotides designed to target viruses can be effective in diminishing viral infection. It is preferred that oligonucleotides have between about 5 and about 50 nucleotide units. It is also preferred that the oligonucleotides be specifically hybridizable with the HCV 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence or 3' end hairpin loop. The oligonucleotide may be modified to increase nuclease resistance and to increase its efficacy.

In accordance with preferred embodiments, the viral RNA is interfered with to an extent sufficient to inhibit HCV infection and/or HCV replication. Thus, oligonucleotides which are capable of interacting with portions of HCV RNA are comprehended. Animals suspected of having HCV-associated disease are contacted with an oligonucleotide made in accordance with this invention. In particular, the present invention is believed to be effective in the treatment of acute and chronic HCV infections and HCV-associated disease, either prophylactically or therapeutically.

It is to be expected that differences in the RNA of HCV from different strains and from different types within a strain exist. Thus, it is believed, for example, that the regions of the various HCV strains serve essentially the same function for the respective strains and that interference with expression of the genetic information will afford similar results in the various strains. This is believed to be so even though differences in the nucleotide sequences among the strains exist.

Accordingly, nucleotide sequences set forth in the present specification will be understood to be representational for the particular strain being described. Homologous or analogous sequences for different strains of HCV are specifically contemplated as being within the scope of this invention.

DETAILED DESCRIPTION OF PREFERRED EMBODIMENTS

Antisense oligonucleotides hold great promise as therapeutic agents for the treatment of many human diseases. In most cases, oligonucleotides complementary to specific RNA target sequences bind by Watson-Crick base pairing to pre-mRNA or mature mRNA, inhibiting the flow of genetic information rom DNA to protein. In the case of RNA viruses such as HCV, oligonucleotides are designed to specifically hybridize to viral genomic RNA, mRNA, or replicative intermediate RNA, interfering with the function of the RNA such that viral replication or protein expression is modulated.

Numerous recent studies have documented the utility of antisense oligonucleotides as biochemical tools for studying target proteins. Rothenberg et al., *J. Natl. Cancer Inst.* 1989, 81, 1539–1544; Zon, G. *Pharmaceutical Res.* 1987, 5, 539–549. Because of recent advances in oligonucleotide chemistry, synthesis of nuclease-resistant oligonucleotides, and availability of types of oligonucleotides which exhibit enhanced cell uptake, it is now possible to consider the use of antisense oligonucleotides as a novel form of therapeutics.

For therapeutics, an animal suspected of having an HCV infection or HCV-associated disease is treated by administering oligonucleotides in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as, for example, antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Dosage and frequency will vary depending on, for example, body weight of patient and means of administration. Individual doses will normally range from about 0.001 mg to 500 mg, but may be higher or lower. Persons of ordinary skill can easily determine optimum dosages, dosing methodologies and repetition rates.

The present invention employs oligonucleotides complementary to specific regions of HCV RNA for antisense inhibition of HCV. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D. U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl, halogen or otherwise substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Modified or unusual bases may also be used; most preferred among these is inosine, which is a "universal base" capable of Watson-Crick pairing with A, C, G or T. Other universal bases may also be preferred. Thus, in one embodiment, the oligonucleotides of this invention have a universal base at a position which is complementary to a nucleotide in the HCV RNA which is variable among strains of HCV.

All such oligonucleotides are comprehended by this invention so long as they function effectively to hybridize with HCV RNA. The oligonucleotides in accordance with this invention preferably comprise from about 5 to about 50 nucleic acid base units. It is more preferred that such oligonucleotides comprise from about 8 to 30 nucleic acid base units, and still more preferred to have from about 14 to 26 nucleic acid base units. As will be appreciated, a nucleic acid base unit is a base-sugar combination suitably bound to adjacent nucleic acid base unit through phosphodiester or other bonds.

In preferred embodiments, the antisense oligonucleotides are complementary to and hybridizable with at least a portion of the loop B region or loop C region of the 5'-untranslated region of the HCV RNA. Particularly suitable antisense oligonucleotides comprises, for example, SEQ ID NO: 33, SEQ ID NO: 41, SEQ ID NO: 20, SEQ ID NO: 38, SEQ ID NO: 39, SEQ ID NO: 40, SEQ ID NO: 42, SEQ ID NO: 44, and SEQ ID NO: 45.

In a preferred embodiment, the antisense oligonucleotides are complementary to and hybridizable with at least a portion of the loop F region of the 5'-end untranslated region of an HCV RNA. Particularly suitable antisense oligonucleotide comprises SEQ ID NO: 62.

In a preferred embodiment, the antisense oligonucleotides are hybridizable with the following nucleotide sequence (A) which is present at the 5'-untranslated region of the HCV genome, or with a nucleotide sequence which is highly homologous to said nucleotide sequence, differing from said nucleotide sequence (A) merely in one or two base units:

(A) GCCUCCAGGACCCC (SEQ ID NO: 97).

Such oligonucleotides are at least 14 nucleotides long, preferably 14 to 26 nucleotides long. Thus, the oligonucleotides contain at least an antisense nucleotide sequence to said nucleotide sequence (A).

More preferable oligonucleotides have a nucleotide sequence which is hybridizable to said nucleotide sequence and further contains a nucleotide sequence complementary to the following nucleotide sequence (B) comprising nucleotides –04–129 of the 5'-end untranslated region of an HCV RNA which are originated from HCV genome or to a continuous nucleotide sequence of about 20 mer within the nucleotide sequence B:

(B) CGUGCAGCCUCCAGGACCCCCCUCC (SEQ ID NO: 98).

(region in bold is equivalent to sequence (A) above).

In other preferred embodiments, the oligonucleotides are hybridizable with at least a portion of the polyprotein translation initiation codon or with at least a portion of the core protein coding region. In a more preferred embodiment, the oligonucleotides contain an antisense nucleotide sequence GGAT which is specifically hybridizable with a nucleotide sequence AUCC of the genome of HCV or neighbor thereof, which is present at nucleotides 352 to 355 in the core protein coding region near the polyprotein translation initiation codon. Suitable examples of the oligonucleotides hybridizable with at least a portion of the polyprotein translation initiation codon are SEQ ID NO: 81, SEQ ID NO: 82, SEQ ID NO: 72, SEQ ID NO: 76, SEQ ID NO: 77, SEQ ID NO: 78, SEQ ID NO: 79, and SEQ ID NO: 80, and suitable examples of the oligonucleotides hybridizable with at least a portion of the core protein coding region of an HCV RNA are SEQ ID NO: 84, SEQ ID NO: 85, SEQ ID NO: 86, SEQ ID NO: 87, SEQ ID NO: 88, SEQ ID NO: 89, SEQ ID NO: 90, and SEQ ID NO: 91. Besides, suitable examples of the oligonucleotides hybridizable with a nucleotide sequence of the nucleotide number 352 to 355 (AUCC) of HCV DNA or neighbor thereof are SEQ ID NO: 76, SEQ ID NO: 77, SEQ ID NO: 78, SEQ ID NO: 79, SEQ ID NO: 80, SEQ ID NO: 84, SEQ ID NO: 85, SEQ ID NO: 86 and SEQ ID NO: 87.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer.

It is also well known to use similar techniques to prepare other oligonucleotides such as the phosphorothioates and alkylated derivatives.

In accordance with this invention, persons of ordinary skill in the art will understand that messenger RNA includes not only the sequence information to encode a protein using the three letter genetic code, but also associated ribonucleotides which form regions known to such persons as the 5'-untranslated region, the 3'-untranslated region, and the 5' cap region, as well as ribonucleotides which form various secondary structures. Thus, oligonucleotides may be formulated in accordance with this invention which are targeted wholly or in part to these associated ribonucleotides as well as to the coding ribonucleotides. In preferred embodiments, the oligonucleotide is specifically hybridizable with the HCV 5' end hairpin loop, 5' end 6-base-pair repeats, ORF 3 translation initiation codon (all of which are contained in the 5'-untranslated region), polyprotein translation initiation codon, core protein coding region, 3'-untranslated region, R2 region, 3' hairpin loop or 3' end palindrome region.

The size of the HCV genome is approximately 9400 nucleotides, with a single translational reading frame encoding a polyprotein which is subsequently processed to several structural and non-structural proteins.

Several regions of the HCV genome have been identified as antisense targets in the present invention. It should be noted that sequence availability and nucleotide numbering schemes vary from strain to strain. The 5' untranslated region of HCV consists of approximately 350 nucleotides upstream of the polyprotein translation initiation codon. A hairpin loop present at nucleotides 1–22 at the 5' end of the genome (HCV-1) identified herein as the "5' end hairpin loop" is believed to serve as a recognition signal for the viral replicase or nucleocapsid proteins. Han et al., *Proc. Natl. Acad. Sci.* 1991, 88, 1711–1715. The 5' untranslated region is believed to have a secondary structure which includes six stem-loop structures, designated loops A–F. Loop A is present at approximately nucleotides 13–50, loop B at approximately nucleotides 51–88, loop C at approximately nucleotides 100–120, loop D at approximately nucleotides 147–162, loop E at approximately nucleotides 163–217, and loop F at approximately nucleotides 218–307. Tsukiyama-Kohara et al., *J. Virol.* 1992, 66, 1476–1483. These structures are well conserved between the two major HCV groups.

Three small (12–16 amino acids each) open reading frames (ORFs) are located in the 5'-untranslated region of HCV RNA. These ORFs may be involved in control of translation. The ORF 3 translation initiation codon as denominated herein is found at nucleotides 215–217 of HCV-1 according to the scheme of Han et al., *Proc. Natl. Acad. Sci.* 1991, 88, 1711–1715; and at nucleotides −127 to −125 according to the scheme of Choo et al., *Proc. Natl. Acad. Sci.* 1991, 88, 2451–2455.

The polyprotein translation initiation codon as denominated herein is an AUG sequence located at nucleotides 342–344 of HCV-1 according to Han et al., *Proc. Natl. Acad. Sci.* 1991, 88, 1711–1715 or at nucleotide 1–3 according to the HCV-1 numbering scheme of Choo et al., *Proc. Natl. Acad. Sci.* 1991, 88, 2451–2455. Extending downstream (toward 3' end) from the polyprotein AUG is the core protein coding region.

The 3' untranslated region, as denominated herein, consists of nucleotides downstream of the polyprotein translation termination site (ending at nt 9037 according to Choo et al.; nt 9377 according to schemes of Han and Inchauspe). Nucleotides 9697–9716 (numbering scheme of Inchauspe for HCV-H) at the 3' terminus of the genome within the 3' untranslated region can be organized into a stable hairpin loop structure identified herein as the 3' hairpin loop. A short nucleotide stretch (R2) immediately upstream (nt 9691–9696 of HCV-H) of the 3' hairpin, and denominated herein "the R2 sequence", is thought to play a role in cyclization of the viral RNA, possibly in combination with a set of 5' end 6-base-pair repeats of the same sequence at nt 23–28 and 38–43. (Inchauspe et al., *Proc. Natl. Acad. Sci.* 1991, 88, 10292–10296) is identified herein as "5' end 6-base-pair repeat". Palindrome sequences present near the 3' end of the genome (nucleotides 9312–9342 according to the scheme of Takamizawa et al., *J. Virol.* 1991, 65, 1105–1113) are capable of forming a stable secondary structure. This is referred to herein as the 3' end palindrome region.

Oligonucleotides useful in the invention are complementary to HCV RNA. Thus, the oligonucleotides whose sequences are shown in Table 1 are believed to be useful against HCV. It is preferred to employ any of these oligonucleotides, or an effective portion thereof, as set forth above, or any of the similar oligonucleotides which persons of ordinary skill in the art can prepare from knowledge of the preferred antisense targets for the modulation of HCV infection.

TABLE 1

RNA SEQUENCE TARGETS AND ANTISENSE OLIGONUCLEOTIDES FOR HCV
[Sequences are from HCV-1 (US) and HCV-J (Japan)]

| SEQ ID NO: | Antisense oligo sequence: | Target description: | Target strand: |
|---|---|---|---|
| 1 | 5'-ATG GTG GAG TGT CGC CCC GTC-3' | 5' end hairpin | + |
| 2 | 5'-GGA GTG ATC TAT GGT GGA GTG-3' | 5' end 6-bp repeat | + |
| 3 | 5'-GAT TCG TGC TCA TGG TGC ACG-3' | Polyprotein AUG | + |
| 4 | 5'-TCC AGG CAT TGA GCG GGT TGA-3' | ORF 3 AUG | + |
| 5 | 5'-TGG CCT GGA GTG TTT ATC TCC-3' | 3'-untranslated | + |
| 6 | 5'-GGG GTA GGC ATC TAC CTG CTC-3' | 3' palindrome | − |
| 7 | 5'-CGC CCC CAT CAG GGG GCT GGC-3' | 5' end hairpin | + |
| 8 | 5'-TTC ATG GTG GAG TGT CGC CCC-3' | 5' end hairpin | + |
| 9 | 5'-GTT CCT CAC AGG GGA GTG ATT-3' | 5' untranslated | + |
| 10 | 5'-TAC TAA CGC CAT GGC TAG ACG-3' | 5' untranslated | + |
| 11 | 5'-CTA TGG CTC TCC CGG GAG GGG-3' | 5' untranslated | + |
| 12 | 5'-CCA CTA TGG CTC TCC CGG GAG-3' | 5' untranslated | + |

TABLE 1-continued

RNA SEQUENCE TARGETS AND ANTISENSE OLIGONUCLEOTIDES FOR HCV
[Sequences are from HCV-1 (US) and HCV-J (Japan)]

| SEQ ID NO: | Antisense oligo sequence: | Target description: | Target strand: |
|---|---|---|---|
| 13 | 5'-CGG TGT ACT CAC CGG TTC CGC-3' | 5' untranslated | + |
| 14 | 5'-CTG GCA ATT CCG GTG TAC TCA-3' | 5' untranslated | + |
| 15 | 5'-GGG GCA CGC CCA AAT CTC CAG-3' | 5' untranslated | + |
| 16 | 5'-CCT TTC GCG ACC CAA CAC TAC-3' | 5' untranslated | + |
| 17 | 5'-CCC TAT CAG GCA GTA CCA CAA-3' | 5' untranslated | + |
| 18 | 5'-CTC CCG GGG CAC TCG CAA GCA-3' | 5' untranslated | + |
| 19 | 5'-CAT GGT GCA CGG TCT ACG AGA-3' | Polyprotein AUG | + |
| 20 | 5'-GTC CTG GAG GCT GCA CGA CA-3' | 5' untranslated | + |
| 21 | 5'-TTT AGG ATT CGT GCT CAT GGT-3' | Polyprotein AUG | + |
| 22 | 5'-GAG TGG TTA GCC CAA TCT TCA-3' | 3' untranslated | + |
| 23 | 5'-TAT TGG CCT GGA GTG GTT AGC-3' | R2 | + |
| 24 | 5'-AGG GAA TGG CCT ATT GGC CTG-3' | R2/3' hairpin | + |

The oligonucleotides of this invention can be used in diagnostics, therapeutics and as research reagents and kits. Since the oligonucleotides of this invention hybridize to RNA from HCV, sandwich and other assays can easily be constructed to exploit this fact. Provision of means for detecting hybridization of oligonucleotide with HCV or HCV RNA present in a sample suspected of containing it can routinely be accomplished. Such provision may include enzyme conjugation, radiolabelling or any other suitable detection systems. Kits for detecting the presence or absence of HCV may also be prepared.

The following specific examples are given for illustrative purposes only and are not intended to limit the invention.

EXAMPLES

Example 1

Oligonucleotide Synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

2'-O-propyl oligonucleotides were prepared from 2'-deoxy-2'-O-propyl ribosides of nucleic acid bases A, G, U(T), and C which were prepared by modifications of literature procedures described by B. S. Sproat, et al., *Nucleic Acids Research* 18:41–49 (1990) and H. Inoue, et al., *Nucleic Acids Research* 15:6131–6148 (1987).

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0.

Example 2

Transcription and Translation of HCV RNA in Genetically Engineered Cells

A recombinant DNA vector capable of expressing HCV genes in mammalian cells is constructed using standard genetic engineering methods. A cDNA fragment representing the HCV mRNA or genomic transcript is placed behind an inducible eukaryotic promotor such as the LTR from mouse mammary tumor virus in such a way that transcription of the HCV cDNA begins at the appropriate nucleotide position. At the 3' end of the gene, a polyadenylation signal is incorporated to ensure termination at the appropriate nucleotide position. It may be advantageous to modify the coding sequence by insertion of an in-frame reporter domain (e.g., the enzymatically active domain of the firefly luciferase gene) which can simplify detection procedures for expression of the fusion protein. The vector also contains one or more selectable genetic markers such as neomycin resistance.

The described vector is introduced into mammalian cells using a standard calcium chloride transfection procedure. Cells containing transfected DNA are identified by growth in the presence of selective agents such as neomycin, and cloned by limiting dilution. Expression of HCV RNA in cloned transfectants can be verified using any one of a number of assays such as northern blots, RNA polymerase chain reaction, or nuclease protection. Protein expression can be verified using western blotting or immune precipitation with specific HCV antibodies, or by monitoring for the presence of detectable enzymatic activity resulting from the incorporation of an assayable reporter domain. If an inducible promotor such as the MMTV LTR is used in construction of the vector, a glucocorticoid inducer such as dexamethasone should be added to the transfected cells prior to assays in order to induce gene expression.

Example 3

Evaluation of Antisense Oligonucleotide Inhibition of HCV Gene Expression from Genetically Engineered Cells Mammalian cells transfected with expression vectors such as those described in Example 2 are incubated overnight in medium containing antisense oligonucleotides. After oligonucleotide treatment, cells are treated with dexamethasone in order to induce expression of HCV gene products. After a suitable incubation period (4–24 hours) cells are harvested, and expression of specific HCV polypeptide can be detected immunologically using specific antisera in a western blot or immunoprecipitation assay. If the cells contain a vector containing a reporter domain, such as that for firefly luciferase, fused in-frame with the HCV polyprotein, cell extracts can be harvested and evaluated for enzymatic activity of the reporter domain.

Example 4

Transcription and Translation of HCV RNA from Cytoplasmic Virus Vectors

A cDNA fragment representing the HCV mRNA or genomic transcript is placed behind a Vaccinia virus promotor in such a way that transcription of the HCV cDNA begins at the appropriate nucleotide position. At the 3' end of the gene, a polyadenylation signal is incorporated to ensure termination at the appropriate nucleotide position. It may be advantageous in some instances to modify the coding sequence by insertion of an in-frame reporter domain (e.g., the enzymatically active domain of the firefly luciferase gene) which can simplify detection procedures for expression of the fusion protein.

Incorporation of the expression unit into the genome of a cytoplasmic replicating DNA virus such as Vaccinia is facilitated by inclusion of sequences upstream and downstream of the expression unit which are homologous to the Vaccinia virus genome. Co-transfection of vector into Vaccinia virus-infected mammalian cells can result in homologous recombination of vector with Vaccinia. If a suitable enzymatic marker such as β-galactosidase is present at the appropriate recombination site in the virus, then recombinant plaques can be identified by a lack of color under appropriate substrate conditions. Cloned virus can be propagated in appropriate host mammalian cell lines and expression of HCV gene products verified as described in Example 2.

Example 5

Evaluation of Antisense Oligonucleotide Inhibition of HCV Gene Expression from Cytoplasmic Virus Vectors in Mammalian Cells Mammalian cells are incubated overnight in medium containing antisense oligonucleotides. After oligonucleotide treatment, cells are infected with recombinant Vaccinia virus expressing HCV gene products. After a suitable incubation period (4–24 hours) cells are harvested, and expression of specific HCV polypeptide can be detected immunologically using specific antisera in a western blot or immunoprecipitation assay. If the cells contain a vector containing a reporter domain, such as that for firefly luciferase, fused in-frame with the HCV polyprotein, cell extracts can be harvested and evaluated for enzymatic activity of the reporter domain.

Example 6

Evaluation of Antisense Oligonucleotide Inhibition of HCV Particle Assembly in Cells Transfected with HCV Genes or Infected with Cytoplasmic Virus Vectors Expressing HCV Genes HCV genomic RNA and protein are expressed in cells transfected with HCV cDNA expression vectors, or in cells infected with Vaccinia virus vectors expressing the HCV cDNA. It is likely that the RNA genomes and proteins will associate to form HCV-like particles. The presence of these particles can be verified using electron microscopy. To evaluate the effects of oligonucleotides complementary to presumed packaging signals of the viral RNA on particle assembly, specific biochemical assays can be developed to measure the appearance of extracellular particles containing both HCV nucleic acid and proteins.

Mammalian cells transfected with expression vectors such as those described in Example 2 are incubated overnight in medium containing antisense oligonucleotides. After oligonucleotide treatment, cells are treated with dexamethasone in order to induce expression of HCV gene products. After a suitable incubation period (4–24 hours) extracellular fluid from treated cells is harvested, and particles are concentrated by pelleting in the ultracentrifuge. Proteins and nucleic acids are extracted from the pellet and quantitated by northern blot and western blot analysis respectively as described in Examples 4 and 5. A similar procedure could be used to monitor effects of oligonucleotide treatment on virus particle assembly resulting from infection of cells with recombinant Vaccinia virus expressing the HCV polyprotein.

Example 7

Screening of Oligonucleotides by in Vitro Translation Assay

1. Preparation of HCV RNA to be used for Translation in vitro:

An RNA having a sequence homologous to the base number 1–686 of HCV gene nucleotide sequence was prepared in the following manner, wherein the stop codon (TGA) was added to 3'-terminus.

(1) Preparation of Template HCV-cDNA for Polymerase Chain Reaction (PCR):

Based on a cDNA nucleotide sequence prepared by the present inventors by cloning from serum of a Japanese patient of Hepatitis C, said cDNA being possibly coding for full length HCV amino acid sequence, there was cloned a cDNA containing 686 nucleotide sequence which comprised the full length 5'-untranslated region of HCV gene (341 nucleotide sequence) and a core region (345 nucleotide sequence) continued thereto at 5'-terminus by a known technique, and the clone was used as a template for the PCR procedure in the following (3). The nucleotide numbers for this cDNA sequence have been found to correspond well to those of Han et al. (*Proc. Natl. Acad. Sci.* 1991, 88, 1711–1715).

(2) Preparation of a Primer for PCR:

There were prepared a sense primer comprising 41 nucleotide sequence which contained 7 bases including EcoRI cleavage site, 20 bases having a function as T7 promoter and 14 bases (nucleotide number 1–14) of HCV nucleotide sequence in this order from the 5'-terminus, and also an antisense primer comprising 27 nucleotide sequence which contained 9 bases including EcoRI cleavage site, 3 bases which are complementary to the stop codon (TGA) and 15 bases which are complementary to the region of the base number 672–686 of HCV nucleotide sequence in this order from the 5'-terminus by a solid phase phosphoamidite method with Cyclone Plus DNA Synthesizer (manufactured by MilliGen/Biosearch).

(3) Preparation of template DNA for synthesis of RNA by PCR:

By using the cDNA obtained in the above (1) as the template, the PCR (20 cycles) proceeded with the primers of the above (2). The PCR was done under the conditions of denaturation: 94° C. for one minute, annealing: 55° C. for 2 minutes, polymerase reaction: 72° C. for 2 minutes. The thus obtained DNA fragment was treated with EcoRI and inserted into EcoRI site of pUC19, and *E. coli* JM 109 strain was transformed with the resultant recombinant plasmid by a conventional method. By sequencing the part inserted with the recombinant plasmid as to the plural clones in colonies thus obtained by dideoxy method, it was confirmed that the HCV-origin 686 nucleotide sequences inserted by the plasmids from all clones conformed well with the corresponding region of the template cDNA. A plasmid obtained from one of the clones was designated "pUIA1".

(4) Preparation of RNA having a part of the nucleotide sequence of HCV gene:

A fragment inserted with the above nucleotide sequence was taken out from the pUIA1 by treating it with EcoRI, and by using said fragment as a template, an RNA was synthesized with MEGAscript in vitro Transcription Kit (manufactured by Ambion), and thereby there was obtained an RNA fragment having 698 nucleotide sequence which comprised 1–686 nucleotide sequence part of HCV nucleotide sequence, stop codon (UGA) and 9 bases including EcoRI cleavage site in this order from 5'-terminus. This fragment was designated "R-IA-1". The nucleotide sequence of the 686 bases derived from HCV in said R-IA-1 is shown in the accompanying FIG. 1.

2. Synthesis of HCV Core Protein in Cell-free Translation System:

An HCV core protein was translated from R-IA-1 in cell-free system by using a rabbit reticulocyte lysate and the expression was confirmed by ELISA as follows.

(1) Construction of ELISA System for Quantitatively Determining HCV Core Protein:

The core region of HCV was directly expressed in *E. coli* by a conventional method. A mouse was immunized with the expressed protein thus obtained, and two kinds of monoclonal antibodies, RJC4-1 (IgM type) and RJC4-2 (IgG type) were obtained therefrom by treating it by a conventional method. Said monoclonal antibody RJC4-1 was diluted with 10 mM PBS, and the diluted RJC4-1 (concentration 50 μg/ml, 50 μl) was added to each well of MaxiSorp F8 plate (Nunc) and fixed by allowing to stand at 4° C. overnight, and thereafter the remaining antibody solution was removed by suction from the well. A PBS containing 1% calf serum albumin (150 μl) was added to each well and allowed to stand at 4° C. overnight to effect blocking of the antibody and then subjected to washing. The core protein to be tested, prepared above using rabbit reticulocyte extract, was diluted in an appropriate concentration with a PBS containing 1% calf serum albumin, and the diluted core protein (50 μl) was added to each well, and the mixture was subjected to reaction at room temperature for 2 hours and then to washing. Thereafter, the antibody RJC4-2 (50 μl) bound with a horseradish peroxidase was added to each well, and the mixture was subjected to reaction at 37° C. for one hour and then to washing. Lastly, an aqueous solution of 3,3',5,5'-tetramethylbenzidine (50 μl) was added to each well, and the mixture was subjected to reaction at room temperature for 15 minutes, and then the reaction was chilled with in sulfuric acid. Immediately, the absorbance of the reaction mixture at 450 nm was measured. As a result, it was found that the HCV core protein could be determined quantitatively by ELISA.

(2) Expression of HCV core protein with a rabbit reticulocyte lysate:

Each of a solution of R-IA-1 (20 pmol) in TE (10 μl) and a TE (10 μl) containing no RNA was mixed with an aqueous solution of methionine (2 μl) (the final concentration of methionine, 10 μM). To each mixture (12 μl) was added a rabbit reticulocyte lysate (In Vitro Translation Kit, manufactured by STRATAGENE, 20 μl), and the mixture was incubated at 30° C. for 2 hours. The reaction mixture was fold-diluted and then the core protein was quantitatively determined by ELISA. As a result, it was confirmed that the HCV core protein was synthesized in the positive control, but no HCV core protein was found in the negative control.

3. Search of Target Region of Antisense Compounds:

Oligonucleotides complementary to the 5'-untranslated region were screened as follows for ability to inhibit the translation of HCV core protein in vitro.

(1) Preparation of synthetic antisense DNA oligonucleotides:

Antisense oligonucleotides were prepared by a solid phase phosphoamidite method as in Example 1 (for oligonucleotides designated "IA-") or using a Cyclone Plus DNA Synthesizer (manufactured by MilliGen/Biosearch) (for oligonucleotides designated "CAS-"). The product thus obtained was treated with phenol and subjected to ethanol precipitation. The precipitate was dissolved in 10 mM Tris-HCl (pH 8.0)—1 mM EDTA solution for use in the subsequent procedure.

The antisense oligonucleotides were each 20 nucleotides in length. The "CAS-" or "IA-" number used to denominate each sequence refers to the number of the 5'-most nucleotide of the corresponding HCV RNA target sequence shown in the accompanying FIG. 1.

(2) Evaluation of inhibitory activity of the antisense oligonucleotides:

R-IA-1 (20 pmol) and an antisense DNA to be tested (100 pmol) were mixed in TE (the final volume, 10 μl), and the mixture was allowed to stand at room temperature for 10 minutes. To the solution was added 10 mM aqueous methionine solution (2 μl), and further to the mixture (12 μl) was added a rabbit reticulocyte lysate (In Vitro Translation Kit, manufactured by STRATAGENE, 20 μl), and the mixture was incubated at 30° C. for 2 hours. After the reaction was completed, the core protein produced in the reaction mixture was quantitatively determined by ELISA, and there was calculated the ratio of the amount of the core protein in said reaction mixture to that of the core protein produced in the TE containing no antisense DNA. The inhibitory activity (%) was calculated by deducting the above-obtained ratio from 1 (one) and expressing the resultant as a percentage.

(3) Screening for target regions effective for inhibition of the growth of HCV:

Antisense oligonucleotides were synthesized which are complementary to target sequences located at 10-nucleotide intervals from nucleotide 1 to 339 in the HCV RNA 5'-untranslated region. The sequences of these oligonucleotides, CAS-1 through CAS-320, are shown in Table 2.

TABLE 2

Antisense oligonucleotides to HCV

| Oligo | Sequence | SEQ ID NO: |
|---|---|---|
| CAS-1 | GCC CCG AAT CGG GGG CTG GC | 26 |
| CAS-10 | TGG AGT GTC GCC CCC AAT CG | 27 |
| CAS-20 | TGA TCT ATG GTG GAG TGT CG | 28 |
| CAS-30 | CAC AGG GGA GTG ATC TAT GG | 29 |
| CAS-40 | AGT AGT TCC TCA CAG GGG AG | 30 |
| CAS-50 | GCG TGA AGA CAG TAG TTC CT | 31 |
| CAS-60 | GAC GCT TTC TGC GTG AAG AC | 32 |

TABLE 2-continued

Antisense oligonucleotides to HCV

| Oligo | Sequence | SEQ ID NO: |
|---|---|---|
| CAS-70 | GCC ATG GCT AGA CGC TTT CT | 33 |
| CAS-80 | TCA TAC TAA CGC CAT GGC TA | 34 |
| CAS-90 | TGC ACG ACA CTC ATA CTA AC | 35 |
| CAS-100 | TCC TGG AGG CTG CAC GAC AC | 36 |
| CAS-101 | GTC CTG GAG GCT GCA CGA CA | 20 |
| CAS-102 | GGT CCT GGA GGC TGC ACG AC | 37 |
| CAS-104 | GGG GTC CTG GAG GCT GCA CG | 38 |
| CAS-106 | GGG GGG TCC TGG AGG CTG CA | 39 |
| CAS-108 | AGG GGG GGT CCT GGA GGC TG | 40 |
| CAS-110 | GGA GGG GGG GTC CTG GAG GC | 41 |
| CAS-110-I-119 | GGA GGG GGG GIC CTG GAG GC | 42 |
| CAS-110-G-119 | GGA GGG GGG GGC CTG GAG GC | 43 |
| CAS-112 | CGG GAG GGG GGG TCC TGG AG | 44 |
| CAS-114 | CCC GGG AGG GGG GGT CCT GG | 45 |
| CAS-116 | CTC CCG GGA GGG GGG GTC CT | 46 |
| CAS-118 | CTC TCC CGG GAG GGG GGG TC | 47 |
| CAS-120 | GGC TCT CCC GGG AGG GGG GG | 48 |
| CAS-130 | AGA CCA CTA TGG CTC TCC CG | 49 |
| CAS-140 | CCG GTT CCG CAG ACC ACT AT | 50 |
| CAS-150 | GGT GTA CTC ACC GGT TCC GC | 51 |
| CAS-160 | TGG CAA TTC CGG TGT ACT CA | 52 |
| CAS-170 | CCG GTC GTC CTG GCA ATT CC | 53 |
| CAS-180 | AAG AAA GGA CCC GGT CGT CC | 54 |
| CAS-190 | GGG TTG ATC CAA GAA AGG AC | 55 |
| CAS-200 | GGC ATT GAG CGG GTT GAT CC | 56 |
| CAS-210 | CAA ATC TCC AGG CAT TGA GC | 57 |
| CAS-220 | GGG GCA CGC CCA AAT CTq CA | 58 |
| CAS-230 | CAG TCT CGC GGG GGC ACG CC | 59 |
| CAS-240 | ACT CGG CTA GCA GTC TCG CG | 60 |
| CAS-250 | ACC CAA CAC TAC TCG GCT AG | 61 |
| CAS-260 | GCC TTT CGC GAC CCA ACA CT | 62 |
| CAS-270 | GTA CCA CAA GGC CTT TCG CG | 63 |
| CAS-280 | CTA TCA GGC AGT ACC ACA AG | 64 |
| CAS-290 | CGC AAG CAC CCT ATC AGG CA | 65 |
| CAS-300 | CCG GGG CAC TCG CAA GCA CC | 66 |
| CAS-310 | ACG AGA CCT CCC GGG GCA CT | 67 |
| CAS-320 | TGC ACG GTC TAC GAG ACC TC | 68 |

The inhibitory activity of these antisense oligonucleotides was tested using the HCV in vitro core protein translation assay. Oligonucleotide CAS-110, which is complementary to a portion of loop C, was found to cause greater than 80% inhibition and is most preferred. These results are shown in FIG. 2.

(4) Analysis at around the base number 100–130 in more detail:
Additional oligonucleotides which are complementary to the region from nucleotide 100 to 140 of HCV RNA, which includes the loop C region, were synthesized and tested as above. These oligonucleotides are shown in Table 2. As shown in FIG. 2, oligonucleotides CAS-104, CAS-106, and CAS-108 were found to inhibit HCV core protein translation in vitro by 70% or more and are preferred. The antisense oligonucleotides complementary to the 26-base region of HCV RNA from nucleotides 104 to 129 showed strong inhibitory activity against the translation of the HCV-RNA in comparison with the antisense oligonucleotides complementary to other regions of 5'-untranslated region. oligonucleotides hybridizable with this region are therefore preferred.

(5) Evaluation of antisense oligonucleotides wherein the base number 119 was substituted by inosine:
Because the nucleotide at position 119 in the loop C region has a high variation rate among HCV strains, various antisense oligonucleotides were prepared wherein the adenosine at this position was substituted by the "universal base" inosine in order to evaluate whether the substituted oligonucleotides would be effective for the inhibition of various virus strains as follows.

Among the nucleotide sequence of CAS-110, the thymidine corresponding to adenosine at nucleotide number 119 was replaced by inosine to give CAS-110-I-119. As a reference, there was also prepared CAS-110-G-119 wherein said thymidine was replaced by guanosine so as to make an artificial mismatch. These sequences are shown in Table 2. The inhibitory activity of these oligonucleotides was evaluated as above. As a result, CAS-110-I-119 showed an inhibitory activity of more than 70% similar to CAS-110, but CAS-110-G-119 showed much lower activity. CAS-110-I-119 is therefore preferred. It is likely from the result that the compound obtained by replacing thymidine with inosine would be effective against other virus strains in which adenosine at position 119 is replaced by another nucleotide.

(6) Evaluation of 2'-O-methyl antisense oligonucleotides:
The binding affinity of antisense oligonucleotides for their target sequence is enhanced by methoxylation of the 2'-position of the sugar moiety in the antisense oligonucleotide. 2'-O-methylated oligonucleotides were prepared having the sequences shown in Table 2 (other than the two substituted by inosine) and their inhibitory activity was evaluated. In most cases, 2'-O-methylated oligonucleotides were similar in inhibitory activity to their unmodified counterparts. Some oligonucleotides (CAS-80, CAS-360) appeared to be less active when 2'-O-methylated, and CAS-260 hybridizing to the loop F region appeared to be significantly more active when 2'-O-methylated, showing greater than 75% inhibition. This sequence is therefore preferred. Activities of some of the tested oligonucleotides are shown in FIG. 3.

Example 8

Evaluation of Inhibitory Activity of Antisense Oligonucleotides Which are Complementary to the Nucleotide Sequence at Around the Polyprotein Translation Initiation Codon and Adjacent Core Protein Coding Region:

(1) In order to evaluate the inhibitory activity of antisense oligonucleotides which are complementary to the nucleotide sequence around the translation initiation codon (nucleotide number 342–344) of HCV-RNA and adjacent core protein coding region, a series of 20 mer antisense oligonucleotides were prepared which are complementary to the region from nucleotide 320 to nucleotide 379. Of these, CAS-324 through CAS-344 contain all or part of the sequence CAT which is complementary to the AUG initiation codon itself. The nucleotide sequence of these antisense oligonucleotides are shown in the accompanying Table 3.

TABLE 3

Antisense oligonucleotides to HCV

| Oligo | Sequence | % Inhibition | SEQ ID NO: |
|---|---|---|---|
| CAS-320 | TGC ACG GTC TAC GAG ACC TC | 3 | 68 |
| CAS-322 | GGT GCA CGG TCT ACG AGA CC | 5 | 69 |
| CAS-324 | ATG GTG CAC GGT CTA CGA GA | 31 | 70 |
| CAS-326 | TCA TGG TGC ACG GTC TAC GA | 39 | 71 |
| CAS-328 | GCT CAT GGT GCA CGG TCT AC | 71 | 72 |
| CAS-330 | GTG CTC ATG GTG CAC GGT CT | 38 | 73 |
| CAS-332 | TCG TGC TCA TGG TGC ACG GT | 5 | 74 |
| CAS-334 | ATT CGT GCT CAT GGT GCA CG | 39 | 75 |
| CAS-336 | GGA TTC GTG CTC ATG GTG CA | 98 | 76 |
| CAS-338 | TAG GAT TCG TGC TCA TGG TG | 99 | 77 |
| CAS-340 | TTT AGG ATT CGT GCT CAT GG | 97 | 78 |

TABLE 3-continued

Antisense oligonucleotides to HCV

| Oligo | Sequence | % Inhi- bition | SEQ ID NO: |
|---|---|---|---|
| CAS-342 | GGT TTA GGA TTC GTG CTC AT | 96 | 79 |
| CAS-344 | GAG GTT TAG GAT TCG TGC TC | 99 | 80 |
| CAS-344-i1 | GAG GTT TAG GAT TIG TGC TC | 95 | 81 |
| CAS-344-i3 | GIG GTT TIG GAT TIG TGC TC | 90 | 82 |
| CAS-344-i5 | GIG GTT TIG GAI IIG TGC TC | 51 | 83 |
| CAS-346 | TTG AGG TTT AGG ATT CGT GC | 98 | 84 |
| CAS-348 | CTT TGA GGT TTA GGA TTC GT | 98 | 85 |
| CAS-350 | TTC TTT GAG GTT TAG GAT TC | 99 | 86 |
| CAS-352 | TTT TCT TTG AGG TTT AGG AT | 99 | 87 |
| CAS-354 | GTT TTT CTT TGA GGT TTA GG | 91 | 88 |
| CAS-356 | TGG TTT TTC TTT GAG GTT TA | 86 | 89 |
| CAS-358 | TTT GGT TTT TCT TTG AGG TT | 83 | 90 |
| CAS-360 | CGT TTG GTT TTT CTT TGA GG | 81 | 91 |

The inhibitory activity of these 21 antisense oligonucleotides was evaluated in the same manner as above at the concentration of 40 pmol of antisense oligonucleotides. As shown in Table 3, antisense oligonucleotides CAS-328, CAS-336, CAS-338, CAS-340, CAS-342, CAS-344, CAS-346, CAS-348, CAS-350, CAS-352, CAS-354, CAS-356, CAS-358 and CAS-360 showed an inhibitory activity of greater than 70%, and are preferred. Of these, CAS-336, CAS-338, CAS-340, CAS-342, CAS-344, CAS-346, CAS-348, CAS-350 and CAS-352 showed an extremely high inhibitory activity of over 95% and are most preferred. Among these, CAS-346 through CAS-360 hybridize to the core protein coding region immediately adjacent to the translation initiation codon and are not complementary to the AUG itself, but still showed an extremely high inhibitory activity. On the other hand, the 6 antisense oligonucleotides CAS-324, CAS-326, CAS-328, CAS-330, CAS-332, and CAS-334 are complementary to the translation initiation codon, but showed lower inhibitory activity than the above 9 most active antisense sequences.

The HCV target sequence regions complementary to the above 9 most active antisense oligonucleotides have in common the four nucleotides from number 352 to 355 in the core protein coding region near the polyprotein translation initiation codon. Thus, it is suggested that it is useful to include these four base units in order to inhibit the translation. Accordingly, oligonucleotides comprising the sequence GGAT are preferred embodiments of the invention.

(2) Evaluation of antisense oligonucleotides wherein the nucleotides known to be variable among strains were substituted by inosine:

It is known that in the nucleotide sequences in the core protein coding region near the translation initiation codon, variation of bases among strains occasionally occurs at the nucleotides 350, 351, 352, 356 and 362. Based on this knowledge, it was studied whether substitution of these bases by the "universal base" inosine would be effective for inhibition of various viruses.

There was prepared an antisense DNA by substituting the base at base number 350 in CAS-344 by inosine, which was designated CAS-344-i1. Likewise, there was prepared an antisense DNA wherein three bases at base numbers 350, 356 and 362 were substituted by inosine, which was designated CAS-344-i3, and an antisense DNA wherein five bases at base numbers 350, 351, 352, 356, and 362 were substituted by inosine, which was designated CAS-344-i5. The inhibitory activity of these antisense oligonucleotides was evaluated as in the above (1). As a result, the CAS-344-i1 and CAS-344-i3 showed high inhibitory activity, which suggests that the antisense oligonucleotides having up to about three inosine substituents of sequence CAS-344 may show high inhibitory activity. These oligonucleotides are preferred. Their inhibitory activities are shown in the accompanying Table 3.

Example 9

Evaluation of Antisense DNA in HCV Core Protein Expression Cells:

(1) Preparation of phosphorothioate oligonucleotides:

Because sequences CAS-110, CAS-260, and CAS-344 showed high inhibitory activity as phosphodiesters (P=O) in the test of in vitro translation, the corresponding phosphorothioate (P=S) oligonucleotides were prepared. These oligonucleotides are designated by adding "S" after the name of each parent oligonucleotide, like "CAS-110S", "CAS-260S", and the like. As a negative control, an oligonucleotide having random sequence was prepared.

(2) Preparation of liver cell transformant:

An expression plasmid was prepared by inserting a gene (1.3 kbp) coding for 5' NCR-Core-env region of HCV gene by a conventional method.

The thus prepared expression plasmid was transfected into a human liver cell strain (H8Ad17) by lipofectin method. A chemical resistant strain was selected on the basis of the chemical resistant marker gene (G418) inserted into the expression plasmid, and thereby, there was obtained the desired liver cell transformant which expressed HCV core protein.

(3) Detection system for core protein which was expressed by the liver cell transformant:

The core protein expressed by the liver cell transformant was detected by ELISA method using an anti-HCV core-mouse monoclonal antibody as the solid phase antibody; an anti-HCV human polyclonal antibody as the primary antibody; and an HRP (horseradish peroxidase)-conjugated anti-human IgG-mouse monoclonal antibody as the secondary antibody. By using this detection system, the core protein expressed by the liver cell transformant was measured.

(4) Evaluation of antisense oligonucleotides:

The liver cell transformant ($2.5 \times 10^5$ cells) were inoculated on 6-well plates, and the cells were fixed thereon. To each plate was added each of the above-obtained five antisense oligonucleotides (each in a concentration of 5 µM). After two days, the cells were harvested and counted. The cells were washed once and lysed with a cell lytic agent, and then, the inhibitory activity was measured by ELISA method.

Setting that the inhibition rate 0% corresponds to the amount of the core protein in case of no addition of an antisense compound, the inhibitory activities of the five P=S antisense oligonucleotides were calculated. As a result, all of the CAS-110S, CAS-260S, CAS-344S and CAS-345S showed inhibitory activities of approximately 30–45% in this in vivo assay. The cell toxicity of these antisense oligonucleotides was also checked. As a result, no cell toxicity was observed in all of these antisense oligonucleotides.

Example 10

Evaluation of Oligonucleotides in Modified In vitro Core Protein Translation Assay:

The assay described in Example 7 was modified to eliminate the PCR amplification step by construction of a T7-HCV-core-env fusion plasmid. A T7 expression plasmid was constructed in which the Hind III to Bam HI fragment containing HCV 5' noncoding region-core sequences was inserted into plasmid pGEM4Z. The resulting plasmid was linearized with Bam HI and transcribed by T7 RNA polymerase. $^{35}$S-labeled in vitro translation products were analyzed by SDS-polyacrylamide gel electrophoresis. The optimal amount of T7 RNA transcript for use in translation assays was determined to be approximately 2.2 pmol RNA per reaction. In vitro translation of HCV RNAs of different sizes also yielded products of the expected sizes.

Figure 4:
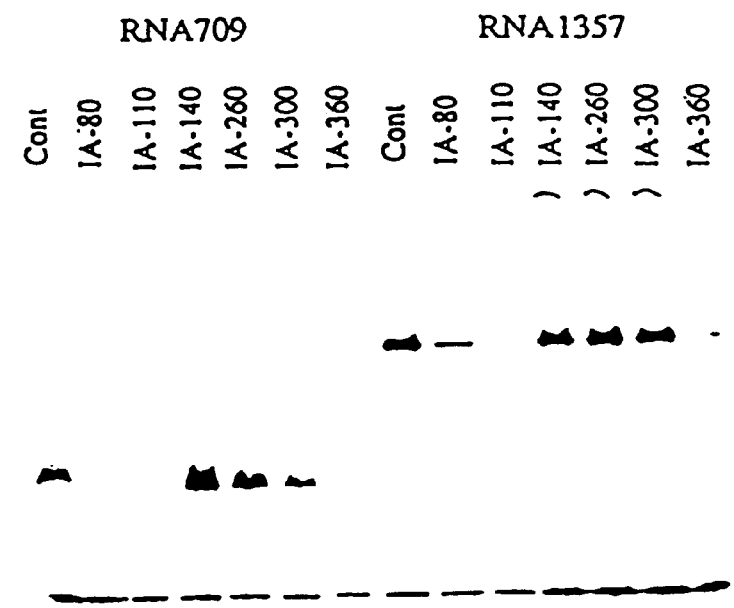
FIG. 4 is an auto radiograph showing inhibitory activities of oligonucleotides IA-80, IA-110, IA-140, IA-260, IA-300 and IA-360 against HCV core protein translation in vitro.

A number of phosphodiester (unmodified) oligonucleotides equivalent to those previously evaluated as described in Example 7 were evaluated in the modified in vitro translation assay. Oligonucleotides were resynthesized and were tested at a molar ration of 20:1. As shown in FIG. 4, oligonucleotides IA-80, IA-110, IA-140 and IA-360 (identical to the previously tested CAS-80, CAS-110, CAS-140 and CAS-360 sequences, respectively; the "IA" or "CAS" prefix indicates different lots synthesized at different facilities) showed activity in the modified assay comparable to that described in the previous examples. Oligonucleotides IA-140, IA-260 and IA-300 (identical to CAS-140, CAS-260 and CAS-300 sequences tested above) did not show good inhibition in this assay. IA-110 and IA-360 showed the best activity and the IA-80 sequence also was inhibitory in this assay, though the degree of inhibition seen with this oligonucleotide was influenced by the RNA template used in the assay.

Figure 5:
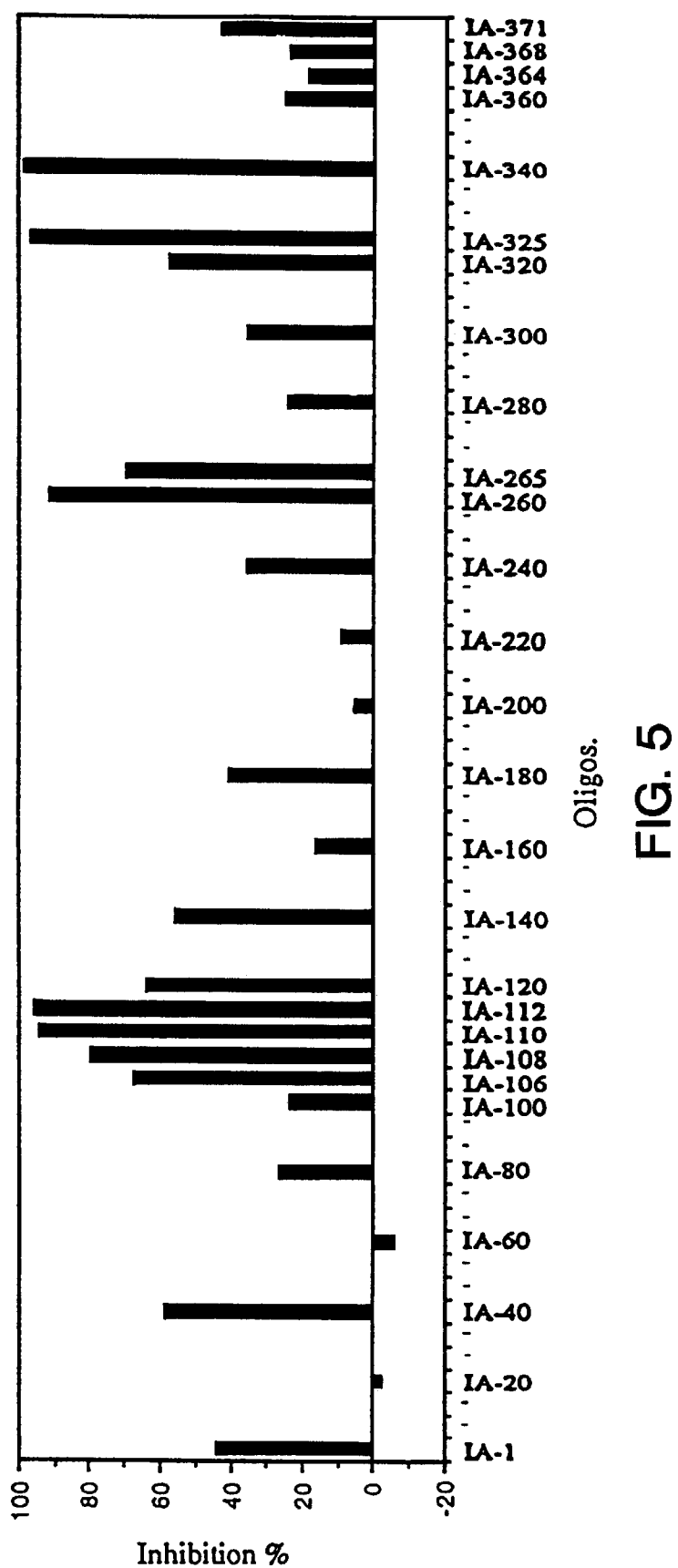
FIG. 5 is a bar graph showing inhibition of HCV core protein translation in the modified in vitro translation assay by oligonucleotides complementary to the region from nucleotide 1 to 371 of HCV RNA.

Oliaonucleotides with 2'-O-methyl Modifications:

Oligonucleotide sequences previously tested as unmodified phosphodiester (P=O) compounds were synthesized as uniform 2'-O-methyl/P=O and tested in the modified in vitro translation assay. Results are shown in FIG. 5. Oligonucleotides IA-110, 112, 260, 325 and 340 showed inhibitory activity in agreement with previous results obtained with P=O oligonucleotides and are preferred. As found using the original assay system, oligonucleotide 260 was more active in 2'-O-methyl/P=O form than as unmodified phosphodiester.

Figure 6:
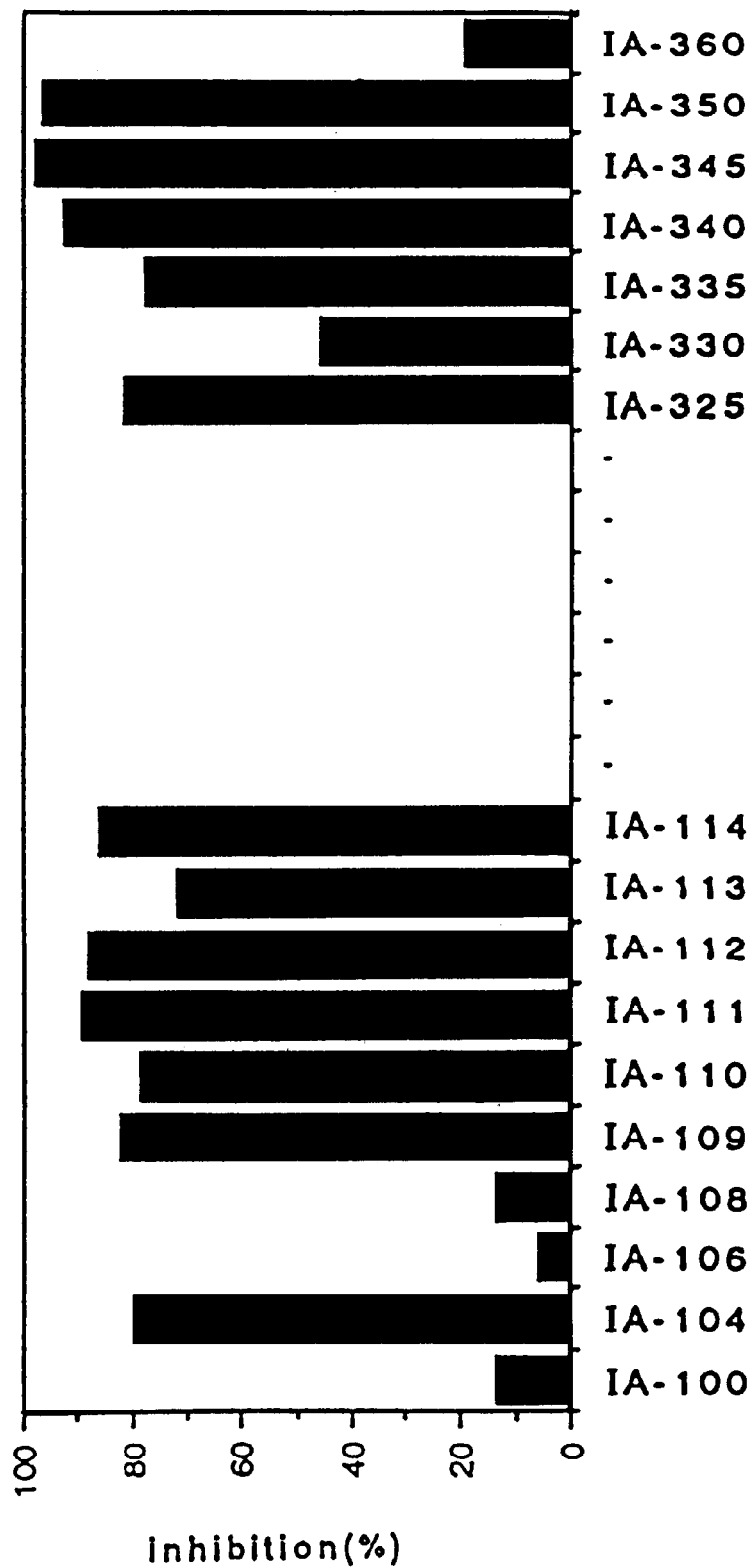
FIG. 6 is a bar graph showing inhibition of HCV translation by 2'-O-methyl/P=O antisense oligonucleotides around the loop C region and AUG codon/core protein coding region.

A panel of uniformly 2'-O-methylated phosphodiester oligonucleotides complementary to loop C sequences was evaluated using the modified in vitro translation assay to identify the oligonucleotide with the greatest inhibitory activity. A second panel of 2'-O-methylated phosphodiester oligonucleotides complementary tc the polyprotein initiation codon region was also tested. The results of these assays are shown in FIGS. 5 and 6. These results confirmed that antisense oligonucleotides complementary to the loop C (around nucleotide 110) and polyprotein translation initiation codon (around nucleotide 340) and adjacent core protein coding region show good inhibitory activity. Such oligonucleotides are preferred.

Evaluation of Phosphorothioate (P=S) Oligonucleotides

Figure 7:
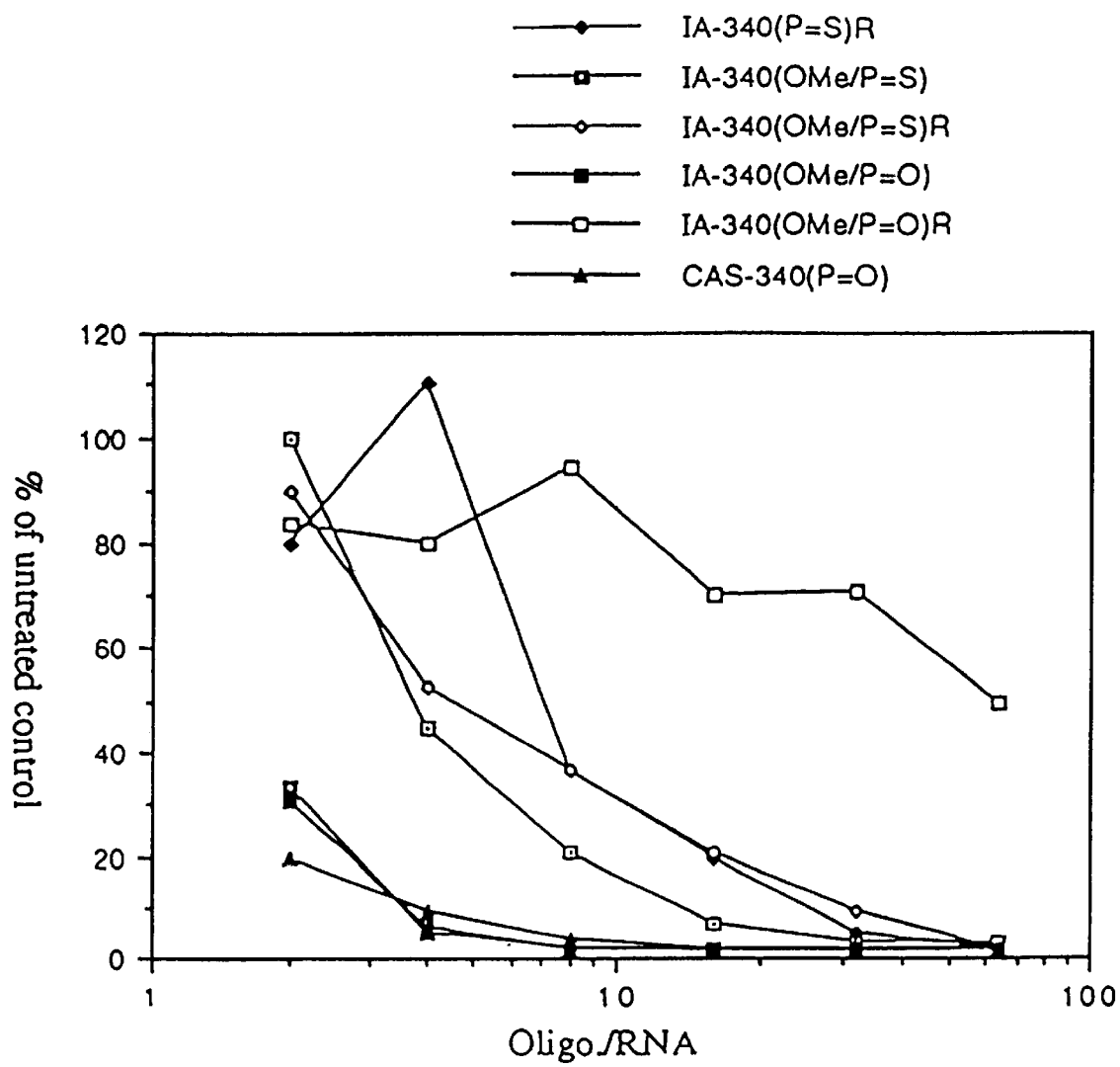
FIG. 7 is a line graph showing dose-dependent inhibition of HCV core protein translation by P=O, P=S, P=O/2'-O—Me and P=S/2'-O—Me versions of IA-340.

Phosphorothioate oligonucleotides IA-110 and IA-340 with 2'-O-methyl modifications throughout were evaluated using the modified in vitro translation assay. A comparison of inhibitory activities of phosphorothioate (P=S), phosphodiester (P=O), 2'-O-me/P=S and 2'-O-me/P=O oligonucleotides was performed. Randomized oligonucleotides (P=S R, 2'-O-Me/P=S R, 2'-O-Me/P=O R) were included in the assays to demonstrate specificity. All IA-110 oligonucleotides, regardless of modification, showed similar ability to inhibit HCV core protein translation. The randomized 110 sequence also showed comparable inhibitory activity, though randomization was not absolute because 13 of the 20 nucleotides in this sequence are G. Oligonucleotide 340 showed sequence-specific inhibition of HCV core protein translation since randomized 340 oligonucleotides showed considerably less inhibitory activity than antisense oligonucleotides. P=O, 2'-O-Me/P=O or 2'-O-Me/P=S oligonucleotides (340 sequence) showed similar near-total reduction in HCV core protein translation which was concentration-dependent, as shown in FIG. 7.

Figure 8:
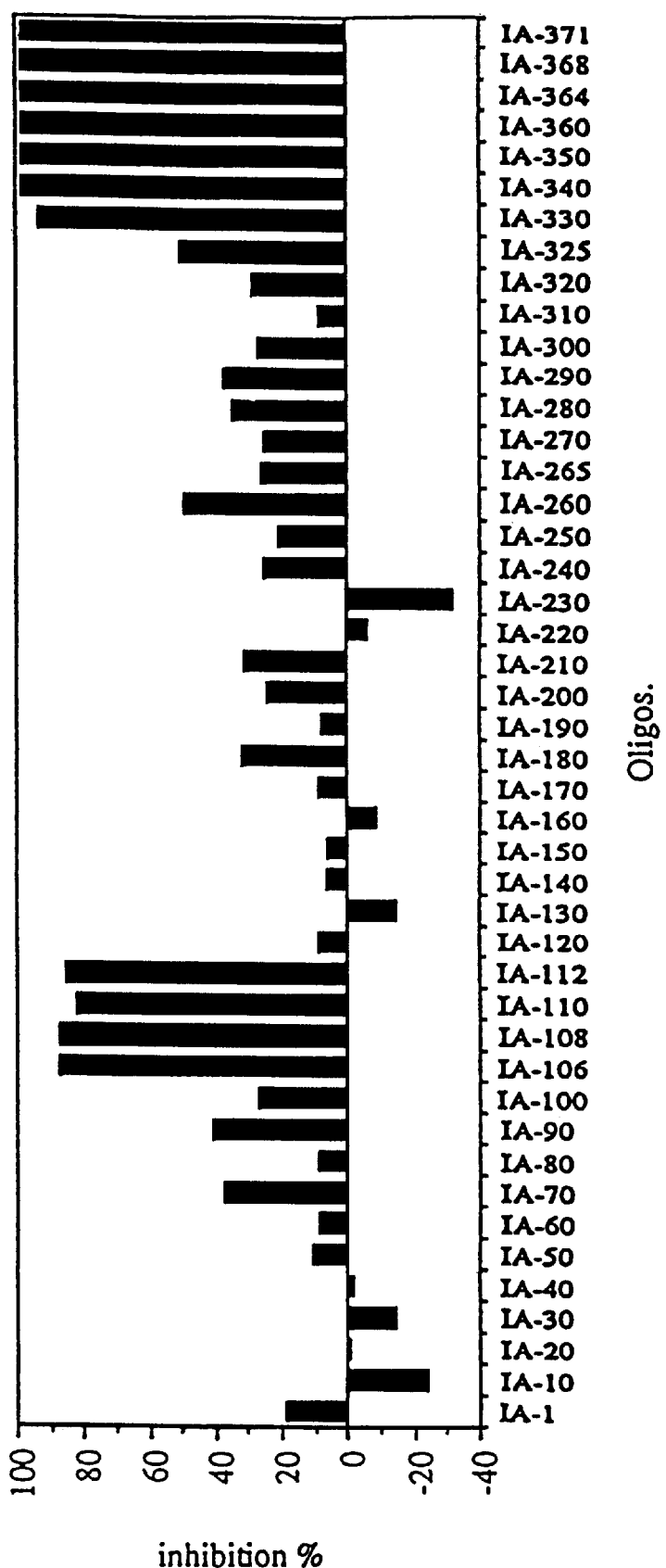
FIG. 8 is a bar graph showing results of a screen of phosphorothioate oligonucleotides by in vitro translation assay after treatment with RNase H.

Because phosphorothioate oligonucleotides tended to show some degree of nonspecific inhibition of in vitro translation in the above assay, a number of phosphorothioates were rescreened in an assay in which RNase H treatment was carried out before the in vitro translation. 2.2 pmol RNA, 4.4 pmol antisense oligonucleotide and 0.23 units RNase H were combined in a total volume of 4 µl in RNase H buffer consisting of 40 mM Tris HCl, pH 8.0, 20 mM MgCl$_2$, 200 mM KCl, and 10% sucrose. The reaction was carried out for 30 minutes at 37° C. In vitro translation and SDS-PAGE were carried out as described in previous examples. RNase H is activated to cleave target RNA only when oligonucleotide is hybridized to the RNA. Both P=O and P=S, but not 2'-O-methyl, oligonucleotides are able to activate RNase H cleavage of RNA. RNA which has been cleaved is not translated into protein. Thus inhibition of translation in this assay indicates successful binding of oligonucleotide to target RNA. Randomized P=S control sequences did not show activity in this assay, demonstrating that they do not bind to the RNA target. Results are shown in FIG. 8.

Example 11

2'-O-propyl and Other Additional Oligonucleotides

Figure 9:
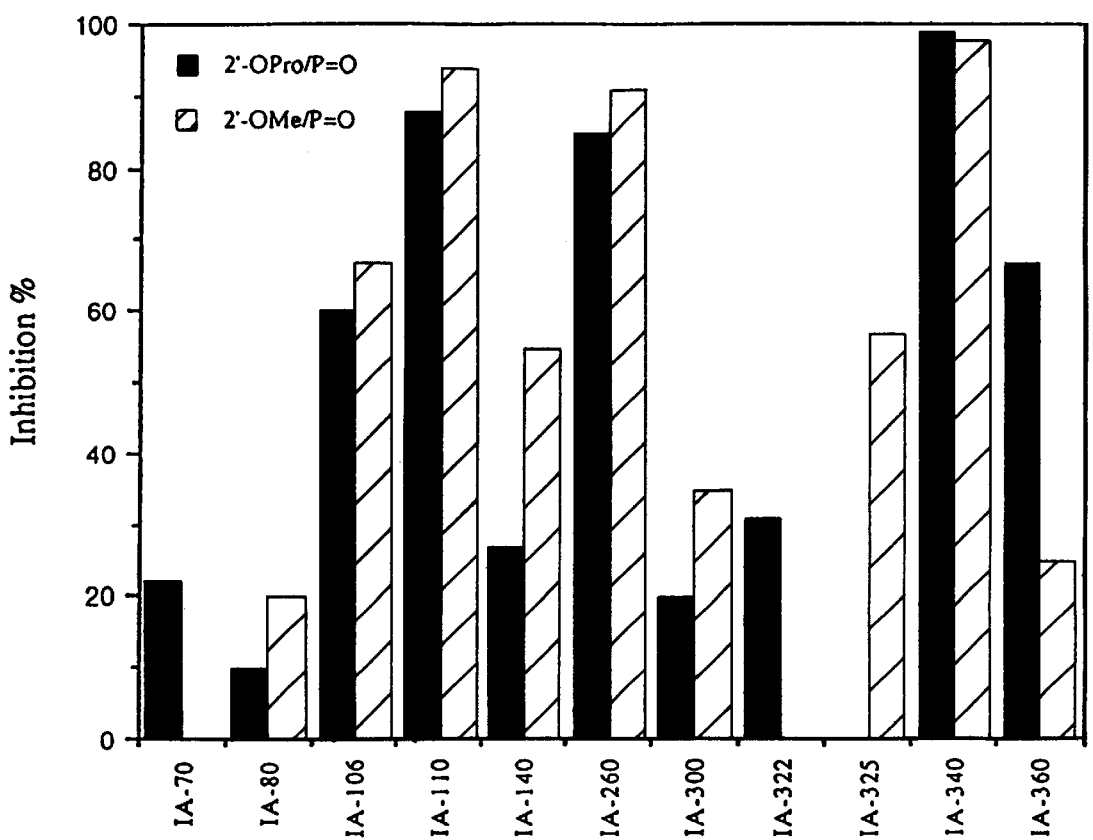
FIG. 9 is a bar graph showing inhibitory activities of 2'-O-propyl and 2'-O-methyl oligonucleotides.

The additional P=S, P=O and 2'-modified oligonucleotides (modified throughout) shown in Table 4 were synthesized. The 2'-O-propyl oligonucleotides were tested in the modified in vitro translation assay and compared to 2'-O-methyl oligonucleotides having the same sequence. As shown in FIG. 9, in most cases the 2'-O-propyl oligonucleotides inhibited HCV core protein translation to approximately the same extent as their 2'-O-methyl counterparts. Most active sequences were IA-110, IA-260 and IA-340; these are preferred embodiments of the invention. In the case of IA-360, the 2'-O-propyl oligonucleotide had greater inhibitory activity than the 2'-O-methyl version.

TABLE 4

Antisense oligonucleotides to HCV

| Oligo | Sequence | Location on HCV | Modifications | | | SEQ ID NO: |
|---|---|---|---|---|---|---|
| IA-1 | GCC CCG AAT CGG GGG CTG GC | 1–19 | P=S | | P=O/2'-OMe | 26 |
| IA-10 | TGG AGT GTC GCC CCC AAT CG | 10–29 | P=S | | | 27 |
| IA-20 | TGA TCT ATG GTG GAG TGT CG | 20–39 | P=S | | P=O/2'-OMe | 28 |
| IA-30 | CAC AGG GGA GTG ATC TAT GG | 30–49 | P=S | | | 29 |
| IA-40 | AGT AGT TCC TCA CAG GGG AG | 40–59 | P=S | | P=O/2'-OMe | 30 |
| IA-50 | GCG TGA AGA CAG TAG TTC CT | 50–69 | P=S | | | 31 |
| IA-60 | GAC GCT TTC TGC GTG AAG AC | 60–79 | P=S | | P=O/2'-OMe | 32 |
| IA-70 | GCC ATG GCT AGA CGC TTT CT | 70–89 | P=S | | P=O/2'-OPro | 33 |
| IA-80 | TCA TAC TAA CGC CAT GGC TA | 80–99 | P=S | P=O | P=O/2'-QMe  P=O/2'-OPro | 34 |
| IA-90 | TGC ACG ACA CTC ATA CTA AC | 90–109 | P=S | | | 35 |
| IA-100 | TCC TGG AGG CTG CAC GAC AC | 100–119 | P=S | | P=O/2'-OMe | 36 |
| IA-106 | GGG GGG TCC TGG AGG CTG CA | 106–125 | P=S | | P=O/2'-OMe  P=O/2'-OPro | 39 |
| IA-108 | AGG GGG GGT CCT GGA GGC TG | 108–127 | P=S | | P=O/2'-OMe | 40 |
| IA-110 | GGA GGG GGG GTC CTG GAG GC | 110–129 | P=S | P=O | P=O/2'-OMe  P=O/2'-OPro | 41 |
| IA-112 | CGG GAG GGG GGG TCC TGG AG | 112–131 | P=S | | P=O/2'-OMe | 44 |
| IA-120 | GGC TCT CCC GGG AGG GGG GG | 120–139 | P=S | | P=O/2'-OMe | 48 |
| IA-130 | AGA CCA CTA TGG CTC TCC CG | 130–149 | P=S | | | 49 |
| IA-140 | CCG GTT CCG CAG ACC ACT AT | 140–159 | P=S | P=O | P=O/2'-OMe  P=O/2'-OPro | 50 |
| IA-150 | GGT GTA CTC ACC GGT TCC GC | 150–169 | P=S | | | 51 |
| IA-160 | TGG CAA TTC CGG TGT ACT CA | 160–179 | P=S | | P=O/2'-OMe | 52 |
| IA-170 | CCG GTC GTC CTG GCA ATT CC | 170–189 | P=S | | | 53 |
| IA-180 | AAG AAA GGA CCC GGT CGT CC | 180–199 | P=S | | P=O/2'-OMe | 54 |
| IA-190 | GGG TTG ATC CAA GAA AGG AC | 190–209 | P=S | | | 55 |
| IA-200 | GGC ATT GAG CGG GTT GAT CC | 200–219 | P=S | | P=O/2'-OMe | 56 |
| IA-210 | CAA ATC TCC AGG CAT TGA GC | 210–229 | P=S | | | 57 |
| IA-220 | GGG GCA CGC CCA AAT CTC CA | 220–239 | P=S | | P=O/2'-OMe | 58 |
| IA-230 | CAG TCT CGC GGG GGC ACG CC | 230–249 | P=S | | | 59 |
| IA-240 | ACT CGG CTA GCG GTC TCG CG | 240–259 | P=S | | P=O/2'-OMe | 60 |
| IA-250 | ACC CAA CAC TAC TCG GCT AG | 250–269 | P=S | | | 61 |
| IA-260 | GCC TTT CGC GAC CCA ACA CT | 260–279 | P=S | P=O | P=O/2'-OMe  P=O/2'-OPro | 62 |
| IA-265 | CAA GGC CTT TCG CGA CCC AA | 265–284 | P=S | | P=O/2'-OMe | 92 |
| IA-270 | GTA CCA CAA GGC CTT TCG CG | 270–289 | P=S | | | 63 |
| IA-280 | CTA TCA GGC AGT ACC ACA AG | 280–299 | P=S | | P=O/2'-OMe | 64 |
| IA-290 | CGC AAG CAC CCT ATC AGG CA | 290–309 | P=S | | | 65 |
| IA-300 | CCG GGG CAC TCG CAA GCA CC | 300–319 | P=S | P=O | P=O/2'-OMe  P=O/2'-OPro | 66 |
| IA-310 | ACG AGA CCT CCC GGG GCA CT | 310–329 | P=S | | | 67 |
| IA-320 | TGC ACG GTC TAC GAG ACC TC | 320–339 | P=S | | P=O/2'-OMe | 68 |
| IA-322 | TGG TGC ACG GTC TAC GAG AC | 322–341 | | | P=O/2'-OPro | 69 |
| IA-325 | CAT GGT GCA CGG TCT ACG AG | 325–344 | P=S | | P=O/2'-OMe | 93 |
| IA-330 | GTG CTC ATG GTG CAC GGT CT | 330–349 | P=S | | | 73 |
| IA-340 | TTT AGG ATT CGT GCT CAT GG | 340–359 | P=S | | P=O/2'-QMe  P=O/2'-OPro | 78 |
| IA-350 | TTC TTT GAG GTT TAG GAT TC | 350–369 | P=S | | | 86 |
| IA-360 | CGT TTG GTT TTT CTT TGA GG | 360–379 | P=S | P=O | P=O/2'-OMe  P=O/2'-OPro | 91 |
| IA-364 | GTT ACG TTT GGT TTT TCT TT | 364–383 | P=S | | P=O/2'-OMe | 94 |
| IA-368 | TGG TGT TAC GTT TGG TTT TT | 368–387 | P=S | | P=O/2'-OMe | 95 |
| IA-371 | GGT TGG TGT TAC GTT TGG TT | 371–390 | P=S | | P=O/2'-OMe | 96 |

P=S: phosphorothioate;
P=O: phosphodiester;
2'-O-Me: 2'-O-methyl;
2'-O-Pro: 2'-O-propyl

What is claimed is:

1. An oligonucleotide which has a nucleotide sequence complementary to at least a portion of a 5' end untranslated region, polyprotein translation initiation codon region or core protein coding region of HCV genomic or messenger RNA, said oligonucleotide inhibiting the function of said RNA and selected from the group consisting of SEQ ID NOs: 1, 2, 4–8, 14, 16, and 21–24.

2. The oligonucleotide of claim 1 in a pharmaceutically acceptable carrier.

3. A method for inhibiting the activity of Hepatitis C virus comprising contacting the virus or cells infected with the virus with an oligonucleotide of claim 1 so that activity of Hepatitis C virus is inhibited.

4. The method of claim 3 wherein said oligonucleotide is in a pharmacuetically acceptable carrier.

5. The method of claim 3 wherein said oligonucleotide has a universal base at a position which is complementary to a nucleotide in the HCV RNA which is variable among strains of HCV.

6. The method of claim 5 wherein the universal base is inosine.

* * * * *

UNITED STATES PATENT AND TRADEMARK OFFICE
CERTIFICATE OF CORRECTION

PATENT NO.    : 6,284,458 B1
DATED         : September 4, 2001
INVENTOR(S)   : Anderson et al.

It is certified that error appears in the above-identified patent and that said Letters Patent is hereby corrected as shown below:

Column 1,
Line 7, please delete "," following -- to --.

Column 4,
Line 12, please delete "rom" and insert -- from --.

Column 6,
Line 29, please delete "-104-129" and insert -- 104-129 --.

Column 19,
Line 50, please delete "tc" and insert -- to --.

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 98

(2) INFORMATION FOR SEQ ID NO: 1:

(i) SEQUENCE CHARACTERISTICS:
      (A) LENGTH: 21
      (B) TYPE: nucleic acid
      (C) STRANDEDNESS: Single
      (D) TOPOLOGY: Linear (iv) ANTI-SENSE: Yes (xi) SEQUENCE DESCRIPTION: SEQ ID NO: 1:

ATGGTGGAGT GTCGCCCCGT C                                              21

(2) INFORMATION FOR SEQ ID NO: 2:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 2:

GGAGTGATCT ATGGTGGAGT G                                              21

(2) INFORMATION FOR SEQ ID NO: 3:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 3:

GATTCGTGCT CATGGTGCAC G                                              21

(2) INFORMATION FOR SEQ ID NO: 4:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 4:

TCCAGGCATT GAGCGGGTTG A                                              21

(2) INFORMATION FOR SEQ ID NO: 5:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 5:

TGGCCTGGAG TGTTTATCTC C                                              21

(2) INFORMATION FOR SEQ ID NO: 6:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 6:

GGGGTAGGCA TCTACCTGCT C                                              21

(2) INFORMATION FOR SEQ ID NO: 7:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 7:

CGCCCCCATC AGGGGGCTGG C        21

(2) INFORMATION FOR SEQ ID NO: 8:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 8:

TTCATGGTGG AGTGTCGCCC C        21

(2) INFORMATION FOR SEQ ID NO: 9:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 9:

GTTCCTCACA GGGGAGTGAT T        21

(2) INFORMATION FOR SEQ ID NO: 10:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 10:

TACTAACGCC ATGGCTAGAC G        21

(2) INFORMATION FOR SEQ ID NO: 11:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 11:

CTATGGCTCT CCCGGGAGGG G        21

(2) INFORMATION FOR SEQ ID NO: 12:

(i) SEQUENCE CHARACTERISTICS:
        (A) LENGTH: 21

(B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 12:

CCACTATGGC TCTCCCGGGA G                                              21

(2) INFORMATION FOR SEQ ID NO: 13:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 13:

CGGTGTACTC ACCGGTTCCG C                                              21

(2) INFORMATION FOR SEQ ID NO: 14:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 14:

CTGGCAATTC CGGTGTACTC A                                              21

(2) INFORMATION FOR SEQ ID NO: 15:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 15:

GGGGCACGCC CAAATCTCCA G                                              21

(2) INFORMATION FOR SEQ ID NO: 16:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 16:

CCTTTCGCGA CCCAACACTA C                                              21

(2) INFORMATION FOR SEQ ID NO: 17:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 17:

CCCTATCAGG CAGTACCACA A                                              21

(2) INFORMATION FOR SEQ ID NO: 18:

(i) SEQUENCE CHARACTERISTICS:
            (A) LENGTH: 21
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 18:

CTCCCGGGGC ACTCGCAAGC A                                              21

(2) INFORMATION FOR SEQ ID NO: 19:

(i) SEQUENCE CHARACTERISTICS:
            (A) LENGTH: 21
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 19:

CATGGTGCAC GGTCTACGAG A                                              21

(2) INFORMATION FOR SEQ ID NO: 20:

(i) SEQUENCE CHARACTERISTICS:
            (A) LENGTH: 21
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 20:

GATTCGTGCT CATGGTGCAC G                                              21

(2) INFORMATION FOR SEQ ID NO: 21:

(i) SEQUENCE CHARACTERISTICS:
            (A) LENGTH: 21
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 21:

TTTAGGATTC GTGCTCATGG T                                              21

(2) INFORMATION FOR SEQ ID NO: 22:

(i) SEQUENCE CHARACTERISTICS:
            (A) LENGTH: 21
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 22:

```
GAGTGGTTAG CCCAATCTTC A                                              21

(2) INFORMATION FOR SEQ ID NO: 23:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 23:

TATTGGCCTG GAGTGGTTAG C                                              21

(2) INFORMATION FOR SEQ ID NO: 24:

(i) SEQUENCE CHARACTERISTICS:
        (A) LENGTH: 21
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 24:

AGGGAATGGC CTATTGGCCT G                                              21

(2) INFORMATION FOR SEQ ID NO: 25:

(i) SEQUENCE CHARACTERISTICS:
        (A) LENGTH: 686
        (B) TYPE: nucleic acid
        (C) STRANDEDNESS: Single
        (D) TOPOLOGY: Linear (iv) ANTI-SENSE: No (xi) SEQUENCE DESCRIPTION: SEQ ID NO: 25:

GCCAGCCCCC GAUUGGGGGC GACACUCCAC CAUAGAUCAC UCCCCUGUGA                50

GGAACUACUG UCUUCACGCA GAAAGCGUCU AGCCAUGGCG UUAGUAUGAG UGUCGUGCA      110

CCUCCAGGAC CCCCCCUCCC GGGAGAGCCA UAGUGGUCUG CGGAACCGGU GAGUACACC      170

GAAUUGCCAG GACGACCGGG UCCUUUCUUG GAUCAACCCG CUCAAUGCCU GGAGAUUUG      230

GCGUGCCCCC GCGAGACUGC UAGCCGAGUA GUGUUGGGUC GCGAAAGGCC UUGUGGUAC      290

GCCUGAUAGG GUGCUUGCGA GUGCCCCGGG AGGUCUCGUA GACCGUGCAC CAUGAGCAC      350

AAUCCUAAAC CUCAAAGAAA AACCAAACGU AACACCAACC GCCGCCCACA GGAGGUCAA      410

UUCCCGGGCG GUGGUCAGAU CGUUGGUGGA GUUUACCUGU UGCCGCGCAG GGGCCCCAG      470

UUGGGUGUGC GCGCGAUCAG GAAGACUUCC GAGCGGUCGC AACCCCGUGG AAGGCGACA      530

CCUAUCCCCA AGGCUCGCCG GCCCGAGGGC AGGGCCUGGG CUCAGCCCGG GUAUCCUUG      590

CCCCUCUAUG GCAAUGAGGG CAUGGGGUGG GCAGGAUGGC UCCUGUCACC CCGCGGCUC      650

CGGCCUAGUU GGGGCCCCAC GGACCCCCGG CGUAGG                              686

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes
```

(xi) SEQUENCE DESCRIPTION: SEQ ID NO: 26:

GCCCCGAATC GGGGGCTGGC                                                    20

(2) INFORMATION FOR SEQ ID NO: 27:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 27:

TGGAGTGTCG CCCCCAATCG                                                    20

(2) INFORMATION FOR SEQ ID NO: 28:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 28:

TGATCTATGG TGGAGTGTCG                                                    20

(2) INFORMATION FOR SEQ ID NO: 29:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 29:

CACAGGGGAG TGATCTATGG                                                    20

(2) INFORMATION FOR SEQ ID NO: 30:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 30:

AGTAGTTCCT CACAGGGGAG                                                    20

(2) INFORMATION FOR SEQ ID NO: 31:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 31:

GCGTGAAGAC AGTAGTTCCT                                                    20

(2) INFORMATION FOR SEQ ID NO: 32:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 32:

GACGCTTTCT GCGTGAAGAC                                       20

(2) INFORMATION FOR SEQ ID NO: 33:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 33:

GCCATGGCTA GACGCTTTCT                                       20

(2) INFORMATION FOR SEQ ID NO: 34:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 34:

TCATACTAAC GCCATGGCTA                                       20

(2) INFORMATION FOR SEQ ID NO: 35:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 35:

TGCACGACAC TCATACTAAC                                       20

(2) INFORMATION FOR SEQ ID NO: 36:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 36:

TCCTGGAGGC TGCACGACAC                                       20

(2) INFORMATION FOR SEQ ID NO: 37:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 37:

GGTCCTGGAG GCTGCACGAC                                                    20

(2) INFORMATION FOR SEQ ID NO: 38:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 38:

GGGGTCCTGG AGGCTGCACG                                                    20

(2) INFORMATION FOR SEQ ID NO: 39:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 39:

GGGGGGTCCT GGAGGCTGCA                                                    20

(2) INFORMATION FOR SEQ ID NO: 40:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 40:

AGGGGGGGTC CTGGAGGCTG                                                    20

(2) INFORMATION FOR SEQ ID NO: 41:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 41:

GGAGGGGGGG TCCTGGAGGC                                                    20

(2) INFORMATION FOR SEQ ID NO: 42:

(i) SEQUENCE CHARACTERISTICS:
        (A) LENGTH: 20
        (B) TYPE: nucleic acid
        (C) STRANDEDNESS: Single (D) TOPOLOGY: Linear (iv) ANTI-SENSE: Yes (xi) SEQUENCE DESCRIPTION: SEQ ID NO: 42:

GGAGGGGGGG NCCTGGAGGC                                                    20

(2) INFORMATION FOR SEQ ID NO: 43:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 43:

GGAGGGGGGG GCCTGGAGGC                                                    20

(2) INFORMATION FOR SEQ ID NO: 44:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 44:

CGGGAGGGGG GGTCCTGGAG                                                    20

(2) INFORMATION FOR SEQ ID NO: 45:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 45:

CCCGGGAGGG GGGGTCCTGG                                                    20

(2) INFORMATION FOR SEQ ID NO: 46:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 46:

CTCCCGGGAG GGGGGGTCCT                                                    20

(2) INFORMATION FOR SEQ ID NO: 47:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 47:

CTCTCCCGGG AGGGGGGGTC                                                    20

(2) INFORMATION FOR SEQ ID NO: 48:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 48:

GGCTCTCCCG GGAGGGGGGG                                                    20

(2) INFORMATION FOR SEQ ID NO: 49:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 49:

AGACCACTAT GGCTCTCCCG                                                    20

(2) INFORMATION FOR SEQ ID NO: 50:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 50:

CCGGTTCCGC AGACCACTAT                                                    20

(2) INFORMATION FOR SEQ ID NO: 51:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 51:

GGTGTACTCA CCGGTTCCGC                                                    20

(2) INFORMATION FOR SEQ ID NO: 52:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 52:

TGGCAATTCC GGTGTACTCA                                                    20

(2) INFORMATION FOR SEQ ID NO: 53:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 53:

CCGGTCGTCC TGGCAATTCC                                          20

(2) INFORMATION FOR SEQ ID NO: 54:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 54:

AAGAAAGGAC CCGGTCGTCC                                          20

(2) INFORMATION FOR SEQ ID NO: 55:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 55:

GGGTTGATCC AAGAAAGGAC                                          20

(2) INFORMATION FOR SEQ ID NO: 56:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 56:

GGCATTGAGC GGGTTGATCC                                          20

(2) INFORMATION FOR SEQ ID NO: 57:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 57:

CAAATCTCCA GGCATTGAGC                                          20

(2) INFORMATION FOR SEQ ID NO: 58:

(i) SEQUENCE CHARACTERISTICS:

(A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 58:

GGGGCACGCC CAAATCTCCA                                          20

(2) INFORMATION FOR SEQ ID NO: 59:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 59:

CAGTCTCGCG GGGGCACGCC                                          20

(2) INFORMATION FOR SEQ ID NO: 60:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 60:

ACTCGGCTAG CAGTCTCGCG                                          20

(2) INFORMATION FOR SEQ ID NO: 61:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 61:

ACCCAACACT ACTCGGCTAG                                          20

(2) INFORMATION FOR SEQ ID NO: 62:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 62:

GCCTTTCGCG ACCCAACACT                                          20

(2) INFORMATION FOR SEQ ID NO: 63:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 63:

GTACCACAAG GCCTTTCGCG                                                      20

(2) INFORMATION FOR SEQ ID NO: 64:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 64:

CTATCAGGCA GTACCACAAG                                                      20

(2) INFORMATION FOR SEQ ID NO: 65:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 65:

CGCAAGCACC CTATCAGGCA                                                      20

(2) INFORMATION FOR SEQ ID NO: 66:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 66:

CCGGGGCACT CGCAAGCACC                                                      20

(2) INFORMATION FOR SEQ ID NO: 67:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 67:

ACGAGACCTC CCGGGGCACT                                                      20

(2) INFORMATION FOR SEQ ID NO: 68:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 68:

TGCACGGTCT ACGAGACCTC                                           20

(2) INFORMATION FOR SEQ ID NO: 69:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 69:

GGTGCACGGT CTACGAGACC                                           20

(2) INFORMATION FOR SEQ ID NO: 70:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 70:

ATGGTGCACG GTCTACGAGA                                           20

(2) INFORMATION FOR SEQ ID NO: 71:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 71:

TCATGGTGCA CGGTCTACGA                                           20

(2) INFORMATION FOR SEQ ID NO: 72:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 72:

GCTCATGGTG CACGGTCTAC                                           20

(2) INFORMATION FOR SEQ ID NO: 73:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 73:

GTGCTCATGG TGCACGGTCT                                           20

(2) INFORMATION FOR SEQ ID NO: 74:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 74:

TCGTGCTCAT GGTGCACGGT                                             20

(2) INFORMATION FOR SEQ ID NO: 75:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 75:

ATTCGTGCTC ATGGTGCACG                                             20

(2) INFORMATION FOR SEQ ID NO: 76:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 76:

GGATTCGTGC TCATGGTGCA                                             20

(2) INFORMATION FOR SEQ ID NO: 77:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 77:

TAGGATTCGT GCTCATGGTG                                             20

(2) INFORMATION FOR SEQ ID NO: 78:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 78:

TTTAGGATTC GTGCTCATGG                                             20

(2) INFORMATION FOR SEQ ID NO: 79:

(i) SEQUENCE CHARACTERISTICS:
        (A) LENGTH: 20

(B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 79:

GGTTTAGGAT TCGTGCTCAT                                           20

(2) INFORMATION FOR SEQ ID NO: 80:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 80:

GAGGTTTAGG ATTCGTGCTC                                           20

(2) INFORMATION FOR SEQ ID NO: 81:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 81:

GAGGTTTAGG ATTNGTGCTC                                           20

(2) INFORMATION FOR SEQ ID NO: 82:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 82:

GNGGTTTNGG ATTNGTGCTC                                           20

(2) INFORMATION FOR SEQ ID NO: 83:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 83:

GNGGTTTNGG ANNNGTGCTC                                           20

(2) INFORMATION FOR SEQ ID NO: 84:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 84:

TTGAGGTTTA GGATTCGTGC                                              20

(2) INFORMATION FOR SEQ ID NO: 85:

(i) SEQUENCE CHARACTERISTICS:
              (A) LENGTH: 20
              (B) TYPE: nucleic acid
              (C) STRANDEDNESS: Single
              (D) TOPOLOGY: Linear (iv) ANTI-SENSE: Yes (xi) SEQUENCE DESCRIPTION: SEQ ID NO: 85:

CTTTGAGGTT TAGGATTCGT                                              20

(2) INFORMATION FOR SEQ ID NO: 86:

(i) SEQUENCE CHARACTERISTICS:
              (A) LENGTH: 20
              (B) TYPE: nucleic acid
              (C) STRANDEDNESS: Single
              (D) TOPOLOGY: Linear (iv) ANTI-SENSE: Yes (xi) SEQUENCE DESCRIPTION: SEQ ID NO: 86:

TTCTTTGAGG TTTAGGATTC                                              20

(2) INFORMATION FOR SEQ ID NO: 87:

(i) SEQUENCE CHARACTERISTICS:
              (A) LENGTH: 20
              (B) TYPE: nucleic acid
              (C) STRANDEDNESS: Single
              (D) TOPOLOGY: Linear (iv) ANTI-SENSE: Yes (xi) SEQUENCE DESCRIPTION: SEQ ID NO: 87:

TTTTCTTTGA GGTTTAGGAT                                              20

(2) INFORMATION FOR SEQ ID NO: 88:

(i) SEQUENCE CHARACTERISTICS:
              (A) LENGTH: 20
              (B) TYPE: nucleic acid
              (C) STRANDEDNESS: Single
              (D) TOPOLOGY: Linear (iv) ANTI-SENSE: Yes (xi) SEQUENCE DESCRIPTION: SEQ ID NO: 88:

GTTTTCTTT GAGGTTTAGG                                               20

(2) INFORMATION FOR SEQ ID NO: 89:

(i) SEQUENCE CHARACTERISTICS:
              (A) LENGTH: 20
              (B) TYPE: nucleic acid
              (C) STRANDEDNESS: Single
              (D) TOPOLOGY: Linear (iv) ANTI-SENSE: Yes (xi) SEQUENCE DESCRIPTION: SEQ ID NO: 89:

```
TGGTTTTTCT TTGAGGTTTA                                          20

(2) INFORMATION FOR SEQ ID NO: 90:

(i) SEQUENCE CHARACTERISTICS:
         (A) LENGTH: 20
         (B) TYPE: nucleic acid
         (C) STRANDEDNESS: Single
         (D) TOPOLOGY: Linear (iv) ANTI-SENSE: Yes (xi) SEQUENCE DESCRIPTION: SEQ ID NO: 90:

TTTGGTTTTT CTTTGAGGTT                                          20

(2) INFORMATION FOR SEQ ID NO: 91:

(i) SEQUENCE CHARACTERISTICS:
         (A) LENGTH: 20
         (B) TYPE: nucleic acid
         (C) STRANDEDNESS: Single
         (D) TOPOLOGY: Linear (iv) ANTI-SENSE: Yes (xi) SEQUENCE DESCRIPTION: SEQ ID NO: 91:

CGTTTGGTTT TTCTTTGAGG                                          20

(2) INFORMATION FOR SEQ ID NO: 92:

(i) SEQUENCE CHARACTERISTICS:
         (A) LENGTH: 20
         (B) TYPE: nucleic acid
         (C) STRANDEDNESS: Single
         (D) TOPOLOGY: Linear (iv) ANTI-SENSE: Yes (xi) SEQUENCE DESCRIPTION: SEQ ID NO: 92:

CAAGGCCTTT CGCGACCCAA                                          20

(2) INFORMATION FOR SEQ ID NO: 93:

(i) SEQUENCE CHARACTERISTICS:
         (A) LENGTH: 20
         (B) TYPE: nucleic acid
         (C) STRANDEDNESS: Single
         (D) TOPOLOGY: Linear (iv) ANTI-SENSE: Yes (xi) SEQUENCE DESCRIPTION: SEQ ID NO: 93:

CATGGTGCAC GGTCTACGAG                                          20

(2) INFORMATION FOR SEQ ID NO: 94:

(i) SEQUENCE CHARACTERISTICS:
         (A) LENGTH: 20
         (B) TYPE: nucleic acid
         (C) STRANDEDNESS: Single
         (D) TOPOLOGY: Linear (iv) ANTI-SENSE: Yes (xi) SEQUENCE DESCRIPTION: SEQ ID NO: 94:

GTTACGTTTG GTTTTTCTTT                                          20

(2) INFORMATION FOR SEQ ID NO: 95:
```

-continued

```
    (i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 95:

TGGTGTTACG TTTGGTTTTT                                          20

(2) INFORMATION FOR SEQ ID NO: 96:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 96:

GGTTGGTGTT ACGTTTGGTT                                          20

(2) INFORMATION FOR SEQ ID NO: 97:

(i) SEQUENCE CHARACTERISTICS:
        (A) LENGTH: 13
        (B) TYPE: nucleic acid
        (C) STRANDEDNESS: Single
        (D) TOPOLOGY: Linear (iv) ANTI-SENSE: No (xi) SEQUENCE DESCRIPTION: SEQ ID NO: 97:

GCCUCCAGGA CCC                                                 13

(2) INFORMATION FOR SEQ ID NO: 98:

(i) SEQUENCE CHARACTERISTICS:
        (A) LENGTH: 26
        (B) TYPE: nucleic acid
        (C) STRANDEDNESS: Single
        (D) TOPOLOGY: Linear (iv) ANTI-SENSE: No (xi) SEQUENCE DESCRIPTION: SEQ ID NO: 98:

CGUGCAGCCU CCAGGACCCC CCCUCC                                   26
```